(12) United States Patent
Barnscheid et al.

(10) Patent No.: US 9,925,146 B2
(45) Date of Patent: *Mar. 27, 2018

(54) OXIDATION-STABILIZED TAMPER-RESISTANT DOSAGE FORM

(71) Applicant: GRÜNENTHAL GMBH, Aachen (DE)

(72) Inventors: Lutz Barnscheid, Mönchengladbach (DE); Eric Galia, Aachen (DE); Sebastian Schwier, Grevenbroich (DE); Ulrike Bertram, Aachen (DE); Anja Geissler, Stolberg (DE); Kornelia Griessmann, Aachen (DE); Johannes Bartholomäus, Aachen (DE)

(73) Assignee: GRÜNENTHAL GMBH, Aachen (DE)

(*) Notice: Subject to any disclaimer, the term of this patent is extended or adjusted under 35 U.S.C. 154(b) by 0 days.

This patent is subject to a terminal disclaimer.

(21) Appl. No.: 14/841,829

(22) Filed: Sep. 1, 2015

(65) Prior Publication Data

US 2015/0366809 A1 Dec. 24, 2015

Related U.S. Application Data

(63) Continuation of application No. 14/192,916, filed on Feb. 28, 2014, now abandoned, which is a continuation of application No. 13/343,846, filed on Jan. 5, 2012, now abandoned, which is a continuation of application No. PCT/EP2010/004461, filed on Jul. 21, 2010.

(30) Foreign Application Priority Data

Jul. 22, 2009 (EP) .................................... 09009480

(51) Int. Cl.
| | | |
|---|---|---|
| A61K 31/44 | (2006.01) | |
| A61K 9/20 | (2006.01) | |
| A61K 9/28 | (2006.01) | |
| A61K 31/485 | (2006.01) | |

(52) U.S. Cl.
CPC .............. *A61K 9/2013* (2013.01); *A61K 9/20* (2013.01); *A61K 9/2031* (2013.01); *A61K 9/2054* (2013.01); *A61K 9/2095* (2013.01); *A61K 9/284* (2013.01); *A61K 31/485* (2013.01)

(58) Field of Classification Search
CPC ...................................................... A61K 31/44
USPC ....................................................... 514/282
See application file for complete search history.

(56) References Cited

U.S. PATENT DOCUMENTS

| | | |
|---|---|---|
| 2,524,855 A | 10/1950 | Schnider et al. |
| 2,806,033 A | 9/1957 | Lewenstein et al. |
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |

(Continued)

FOREIGN PATENT DOCUMENTS

| | | |
|---|---|---|
| AR | 046994 A1 | 12/2004 |
| AR | 045353 A1 | 10/2005 |

(Continued)

OTHER PUBLICATIONS

Waterman et al. (Pharmaceutical Development and Technology vol. 7, pp. 1-32, published 2002).*

(Continued)

*Primary Examiner* — Timothy P Thomas
*Assistant Examiner* — George W Kosturko
(74) *Attorney, Agent, or Firm* — Norris McLaughlin & Marcus, P.A.

(57) ABSTRACT

A thermoformed pharmaceutical dosage form having a breaking strength of at least 300 N, said dosage form comprising
- a pharmacologically active ingredient (A),
- a free physiologically acceptable acid (B) in an amount of from 0.001 wt.-% to 5.0 wt.-%, based on the total weight of the pharmaceutical dosage form, and
- a polyalkylene oxide (C) having a weight average molecular weight $M_w$ of at least 200,000 g/mol.

9 Claims, 1 Drawing Sheet

(56) References Cited

U.S. PATENT DOCUMENTS

| | | |
|---|---|---|
| 4,629,621 A | 12/1986 | Snipes |
| 4,667,013 A | 5/1987 | Reichle |
| 4,690,822 A | 9/1987 | Uemura |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,125,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludgwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,330 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,228,863 B1 | 5/2001 | Palermo |
| 6,235,825 B1 | 5/2001 | Yoshida et al. |
| 6,238,697 B1 | 5/2001 | Kumar et al. |
| 6,245,357 B1 | 6/2001 | Edgren et al. |
| 6,248,737 B1 | 6/2001 | Buschmann et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko |
| 6,375,963 B1 | 4/2002 | Repka et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |

(56) References Cited

U.S. PATENT DOCUMENTS

| | | |
|---|---|---|
| 7,842,307 B2 | 11/2010 | Oshlack et al. |
| 7,851,482 B2 | 12/2010 | Dung et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 9,192,578 B2 | 11/2015 | McGinity et al. |
| 9,629,807 B2 | 4/2017 | Arkenau-Maric et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1* | 9/2002 | Iyer ................ H01L 21/743 438/149 |
| 2002/0176888 A1 | 11/2002 | Bartholomaeus et al. |
| 2002/0187192 A1 | 12/2002 | Joshi et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |
| 2004/0185105 A1 | 9/2004 | Berner et al. |
| 2004/0213845 A1 | 10/2004 | Sugihara |
| 2004/0213848 A1 | 10/2004 | Li et al. |
| 2005/0015730 A1 | 1/2005 | Gunturi et al. |
| 2005/0031546 A1 | 2/2005 | Bartholomaeus et al. |
| 2005/0058706 A1 | 3/2005 | Bartholomaeus et al. |
| 2005/0063214 A1 | 3/2005 | Takashima |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaeus et al. |
| 2005/0181046 A1 | 8/2005 | Oshlack et al. |
| 2005/0186139 A1 | 8/2005 | Bartholomaeus et al. |
| 2005/0191244 A1 | 9/2005 | Bartholomaeus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1* | 3/2007 | Arkenau-Maric ... A61K 9/2027 424/10.1 |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0220079 A1 | 9/2008 | Chen |
| 2008/0233178 A1 | 9/2008 | Reidenberg et al. |
| 2008/0234352 A1 | 9/2008 | Fischer et al. |

(56) References Cited

U.S. PATENT DOCUMENTS

| | | |
|---|---|---|
| 2008/0247959 A1 | 10/2008 | Bartholomaus et al. |
| 2008/0248113 A1 | 10/2008 | Bartholomaus et al. |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0117191 A1 | 5/2009 | Brown Miller et al. |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0321716 A1 | 12/2012 | Vachon et al. |
| 2013/0028970 A1 | 1/2013 | Schwier et al. |
| 2013/0090349 A1 | 4/2013 | Geißler et al. |
| 2013/0129825 A1 | 5/2013 | Billoet et al. |
| 2013/0129826 A1 | 5/2013 | Gei Ler et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wenig et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0374630 A1 | 12/2015 | Arkenau Maric et al. |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AR | 049562 A1 | 8/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 82 | 1/2006 |
| AU | 2005259478 B2 | 1/2006 |
| AU | 2006210145 A1 | 8/2006 |
| AU | 2006210145 B2 | 8/2006 |
| AU | 2009243681 A1 | 1/2009 |
| AU | 2009207796 A1 | 7/2009 |
| AU | 2006311116 B2 | 1/2013 |
| BR | PI0413318 A | 10/2006 |
| BR | PI0413361 A | 10/2006 |
| BR | PI051330 A | 5/2008 |
| BR | PI0606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |

(56) References Cited

FOREIGN PATENT DOCUMENTS

| | | | |
|---|---|---|---|
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 20172004 A1 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101652128 A | 2/2010 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102 04032051 A1 | 1/2006 |
| DE | 102004032049 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1668055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 11/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 113832 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |

(56) References Cited

FOREIGN PATENT DOCUMENTS

| | | |
|---|---|---|
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08051331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2002524150 A | 8/2002 |
| JP | 2002-275175 A | 9/2002 |
| JP | 2003125706 A | 5/2003 |
| JP | 2003526598 A | 9/2003 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009531453 A | 9/2009 |
| JP | 2009537456 A | 10/2009 |
| JP | 2011504455 A | 2/2011 |
| JP | 2011506493 A | 3/2011 |
| JP | 2013536810 A | 9/2013 |
| JP | 2014505736 A | 3/2014 |
| JP | 2014528437 A | 10/2014 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A1 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026262 A2 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |

(56) References Cited

FOREIGN PATENT DOCUMENTS

| | | |
|---|---|---|
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A1 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037230 A1 | 5/2004 |
| WO | WO 2004/037259 A1 | 5/2004 |
| WO | WO 2004/037260 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/131357 A1 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2008/023261 A1 | 2/2008 |
| WO | WO 2008/033523 A1 | 3/2008 |
| WO | WO 2008/069941 A2 | 6/2008 |
| WO | WO 2008/086804 A2 | 7/2008 |
| WO | WO 2008086804 A2 * | 7/2008 | ........... A61K 9/2031 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/128630 A2 | 10/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/059512 A1 | 4/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/103379 A1 | 7/2015 |

OTHER PUBLICATIONS

Freed et al., (International Journal of Pharmaceutics vol. 357, pp. 180-188, published 2008).*
Polyox Water-Soluble Resins in Pharmaceutical Applications. Dow Chemicals. Published 2004 (Year: 2004).*
Extended European Search Report and Opinion for Application No. EP 15165067.8-1455, dated Nov. 2, 2015.
Extended European Search Report and Opinion for Application No. EP 15165065,2-1455, dated Nov. 2, 2015.
Extended European Search Report and Opinion for Application No. EP 15165069.4-1455, dated Nov. 2, 2015.

(56) References Cited

OTHER PUBLICATIONS

Extended European Search Report and Opinion for Application No. EP 15165064,5-1455, dated Oct. 16, 2015.
Extended European Search Report and Opinion for Application No. EP 15165070.2-1455, dated Nov. 2, 2015.
Cuesov, 1999, pp. 351-352.
Sidhu et al., "Watch for nonpsychotropics causing psychiatric side effects," Current Psychiatry, vol. 7, No. 4, 2008, 61-74.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Vynckier et al.,"Hot-melt co-extrusion for the production of fixed-dose combination products with a controlled release ethylcellulose matrix core," International Journal of Pharmaceutics 464 (2014), 65-74.
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Satesh et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Borquist et al., "Simulation of the release from multiparticulate system validated by single pellet and dose release experiments," J. Controlled Release, 97: 453-465 (2004).
Alekseeva et al, Chemical-Pharmaceutical Journal, vol. 41, No. 9, 2007, 49-52. (English abstract included.).
Extended European Search Report and Opinion for Application No. EP 15184634.2-1455, dated Mar. 3, 2016.
Saleem et al. "Formulation and Evaluation of Tramadol hydrochloride Rectal Suppositories," Indian J. Pharm Sci. Sep.-Oct. 2008; 70(5), 640-644.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
Cuesov, Drug Production Technology, Khar'kov, 1999, pp. 351-352.
Efentakis et al, Effects of Excipients on Swelling and Drug Release from Compressed Matrices, in Drug Development and Industrial Pharmacy 23(1):107-112, Jan. 1997, Abstract.
Bingwen et al, 2008, p. 367. (full translation attached).
Bruce et al, Properties of hot-melt extuded tablet formulations for the colonic delivery of 5-aminosalicylic acid, European Journal of Pharmaceutics and Biopharmaceutics, 59 (2005) 85-97.
Extended European Search Report and Opinion for Application No. EP 15153679.4-1455, dated Jun. 30, 2015.
PCT International Search Report and Written Opinion for PCT Application No. PCT/EP2015/060377 dated Jul. 23, 2015.
PCT International Search Report ad Written Opinion for PCT Application No. PCT/EP2015/061343 dated Jul. 21, 2015.
West, Anthony R., Solid state chemistry and its applications, Wiley, New York, 1988, pp. 358 and 365.
Monolithic: retrieved from internet: http:/merriam-webster.com/dictionary/monolithic. Retrieved on Sep. 2, 2015.
2.9 Methoden der pharmazeutischen Technologie, European Pharmacopeia, 143-144, 1997. (Full English translation attached).

Albertini, B. "New spray congealing atomizer for the microencapsulation of highly concentrated solid and liquid substances" European Journal of Pharmaceutics and Biopharmaceutics 69 (2008) 348-357.
Almeida, A. et al., Ethylene vinyl acetate as matrix for oral sustained release dosage forms produced via hot-melt extrusion, European Journal of Pharmaceutics and Biopharmaceutics 77 (2011) 297-305.
Almeida, A. et al., Sustained release from hot-melt extruded matrices based on ethylene vinyl acetate and polyethylene oxide, European Journal of Pharmaceutics and Biopharmaceutics 82 (2012) 526-533.
Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.
Apicella A.et al., Biomaterials, vol. 14, No. 2, pp. 83-90, 1993.
Application of a modelling system in the formulation of extended release hydrophilic matrices, Reprinted from Pharmaceutical Technology Europe, Jul. 2006.
Application of Opadry II, complete film coating system, on metformin HCL extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J. Org Chem. 28(1), pp. 152-155, Abstract 1963.
Avis, Kenneth, Parenteral Preparations. Chapter 85. pp. 1518-1541In Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug. 1987, vol. 102, No. 4, p. 426-429.
Block, Lawrence. Medicated Applications. Chapter 88. In Remington's Pharmaceutical Sciences, 17th Ed, 1985.
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.

(56) References Cited

OTHER PUBLICATIONS

Crowley M.M. et al., "Stability of polyethylene oxide in matrix tablets prepared by hot-metl extrusion," Biomaterials 23, 2002, pp. 4241-4248.
Crowley MM, Drug Dev Ind Pharm. Sep. 2007; 33(9):909-26. (Abstract only).
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Seres), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly, Water Soluble-Resin 2004, pp. 1-2.
Dow Technical Data, Polyox WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53, Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 In Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.
European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708. 1-1219, dated Sep. 24, 2012.
European Search Report and Opinion Application No. 14176277. 3-1460, dated Dec. 15, 2014,.
European Search Report and Opinion, Application No. 11006253. 6-2112, dated Dec. 16, 2011.
European Search Report and Opinion, Application No. 11006254. 4-2112, dated Dec. 16, 2011.
European Search Report and Opinion, Application No. 11008131. 2-1219, dated Feb. 24, 2012.
European Search Report and Opinion, Application No. 11009129. 5-2112, dated Apr. 10, 2012.
European Search Report and Opinion, Application No. 12001296. 8-1219, dated Jun. 26, 2012.
European Search Report and Opinion, Application No. 12001301. 6-1219, dated Jun. 26, 2012.
European Search Report and Opinion, Application No. 12003743. 7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCI (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms (2009).
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).

(56) References Cited

OTHER PUBLICATIONS

Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release, 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33(3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).
Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull 1992, 40(10), 2800-2804.
King et al, Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, $16^{th}$ Edition.
King, Remington's Pharmaceutical Sciences 17th ed., Chapter 78, p. 1418 (1985).
Knevel, Adelbert. Separation. Chapter 78. pp. 1432-1442 In Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 In Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharnaceuticais and Health Care Products"; Blackie Academic & Professional; First Edition 1996. (Table of contents only).
Longer et al. Sustained-Release Drug Delivery Systems. Chapter 92. pp. 1611-1661 In Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al,, "Darstellung wirkstoffhaltiger Extrusionsformlinge auf der Basis von Thermoplasten. Teil 1: Untersuchung zur Wirkstoffliberation" Pharmazie 44, H. 11, pp. 773-776. 1989, English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
McGary, C.W.. Jr. "Degradation of Poly(ethylene Oxide)", Journal of Polymer Science vol. XLVI,1960, pp. 51-57.
McGinity et al., Hot-Melt Extrusion as a Pharmaceutical Process, American Pharmaceutical Review vol. 4 (2), pp. 25-36, 2001.
McGinity, J.W.—Letter of Jan. 26, 2009, pp. 1-4.
McNeill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-963.

(56) References Cited

OTHER PUBLICATIONS

Mesiha M.S. et al "A Screening Study of Lubricants in Wet Powder Passes Suitable for extrusio-spheronization". Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Moorman-Li, R. et al, "A Review of Abuse-Deterrent Opiods for Chronic Nonmalignant Pain." Pharmacy and Therapeutics, vol. 37, No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; In Remington's Pharmaceutical Sciences, 17th Ed, 1985.
Munjal M. et al., "Polymeric Systems for Amorphous Delta$^\wedge$ 9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, In Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.
Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
PCT International Search Report and Written Opinion for PCT Application No. PCT/EP2010/004459 dated Dec. 1, 2010.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Phillips, G. Briggs, Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system. Journal of Controlled Release, 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
Polyox water-soluble resins (DOW Mar. 2002); see http://msds-search.dow.com/PublishedLiteratureDOWCOM/dh_0031/0901b80380031a4a.pdf?filepath=/326-00001.pdf&fromPage=GetDoc).
Polyox WSR-303, retrieved Mar. 10, 2014 from URL http://www.dow.com/dowwolff/en/industrial_solutions/polymers/polyethylene.
Polyox, Colorcon, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.
Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs as First Priority; New Drug Application Delayed," www.headaches.about.com, Jun. 18, 2002, pp. 1-6.

(56) References Cited

OTHER PUBLICATIONS

Quintavalle et al., "Preparation of sustained release co-extrudates by hot-melt extrusion and modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, No. 3, (Jul. 25, 2016). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Salomies et al., "Determination of Oxycodone Hydrochloride in Oral Solutions by High-Performance Thin-Layer Chromatography/ Densitometry," Journal of AOAC International, 83: 1497-1501 (2000).
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).
Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCI From Melt extruded Polyethylene Disks", Pharmaceutical Research, Oct. 1991, vol. 8, No. 10, p. S-192.
Siegel, P. Tonicity, Osmoticity, Osmolality, and Osmolarity. Chapter 80. pp. 1454-1472 In Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents,.
Swarbrick, Encyclopedia of Pharmaceutical Technology, Informa Healthcare, 1988, 1st edition, vol. 9, table of contents.
Tablet, www.docstoc.com (2011).
Third Party Observations filed with EPO for Patent EP65805581, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.

(56) References Cited

OTHER PUBLICATIONS

Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004:2 (1): 43-57.
Vippagunta et al. Crystalline Solids, Advanced Drug Delivery Review 48 (2001), 3-26.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart—N.Y., 1982, pp. 82-92 (Full English Translation attached).
Wagner, Pharmazeutische Biologie—Drofen und ihre Inhaltsstoffe—Scharfstoffdrogen, 2nd., revised edition, Gustav Fischer Verlag, Stuttgart—N.Y., 1982, Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).
Weiss, U., "Derivatives of Morphine. l 14-Dihydroxydihydromorphinone," J. Am. Chem. Soc. 77, pp. 5891-5892, Nov. 20, 1955.
Wikipedia-Dextromethorphan Aug. 12, 2013 (and attached related English-language entry dated Dec. 11, 2013).
Woodburn, K.R. et al., Vascualr complications of injecting drug misuse, Br. J. of Surgery, vol. 83, 1996, pp. 1329-1334.
Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.
Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.
Yarbrough et al, Letters to Nature "Extraordinary effects of mortar-and-pestle grinding on microstructure of sintered alumina gel", Nature 322, pp. 347-349 (Abstract Only) (Jul. 24, 1986).
Yeh et al., Stability of Morphine in Aqueous Solution III: Kinetics of Morphine Degradation in Aqueous Solution, Wiley Subscription Services, Inc., Journal of Pharmaceutical Sciences, 50(1):35-42 (1961).
Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmaSciTech 11(2); 910-916 (available on-line May 22, 2010).
Zhang et al., "Properties of Sustained-Release Tablets Prepared by Hot-Melt Extrusion" Pharmaceutical Development and Technology, 1999, 4(2), 241-250.
Baxter, J.L. et al., "Hydrodynamics-induced variability in the USP apparatus II dissolution test," International Journal of Pharmaceutics 292 (2005) 17-28.
Bellmann et al., "Development of an advanced in vitro model of the stomach and its evaluation versus human gastric psychology." Food Research International 88 (2016) 191-198.
Koziolek, M. et al., "Development of a bio-relevant dissolution test device simulating mechanical aspects present in the fed stomach," European Journal of Pharmaceutical Sciences 57 (2014) 250-256.
Remington, Chapter 45, pp. 996-1035.
Remington, Chapter 45, pp. 996-1035. (Full Translation Attached).
Linz et al. "Cebranopadol: A Novel Potent Analgesic Nociception/Orphanin FQ Peptide and Opioid Receptor Agonist," J Pharmacol. Exp. Ther. 2014; 349: 535-548; available online Apr. 8, 2014.
Decision of the United States District Court for the Southern District of New York, in In re *Endo Pharmaceuticals Inc. and Grunenthal GmbH v. Amneal Pharmaceuticals, LLC et al.*, Findings of Fact and Conclusions of Law, District Judge Thomas P. Griesa, New York, New York, Jan. 14, 2015.
Decision of the United States District Court for the Southern District of New York, in In re *Oxycontin Antitrust Litigation, Purdue Pharma LP v. Teva Pharmaceuticals*, Findings of Fact and Conclusions of Law, District Judge Sidney H. Stein, New York, New York, Jan. 14, 2014.
U.S. Court of Appeals, Federal Circuit, *Purdue Pharma L.P. v. Epic Pharma, LLC*, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes In and Tastes of Paprika," in Taste: Proceedings of the Oxford Symposium on Food and Cookery 28 (Tom Jaine Ed.) 1988, pp. 25-40.
Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with 1 Polyethylene Oxide by Direct Compression," Proceedings of the 29$^{th}$ Annual Meeting of the Controlled Release Society, in collaboration with the Korea Society for Biomaterials, Minneapolis, 1$^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002). Controversies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of the University of Texas at Austin. (May 2003).
Crowley, M., et al., "Evaluation of a Hot Melt Extrusion Technique using a Hydrophilic Thermal Polymer and Retardant for the Prepa-

(56) References Cited

OTHER PUBLICATIONS ration of Extended Release Chlorpheniramine Maleate Tablets," in American Association of Pharmaceutical Scientists: Indianapolis, IN (2000). CROWLEY0000001-CROWLEY0000127.

Davies, N. "Sustained Release and Enteric Coated NSAIDs: Are They Really GI Safe?" J. Pharm. & Pharmaceut. Sci., 2(1):5-14, 1999.

Declaration of Dr. James W. McGinity, dated Oct. 28, 2009; online, retrieved from: http://www.accessdata.fda.gov/dmgsatfda_docs/labeV2013/021121s032lbl.pdf.

Dimitrov, M, et al., "Study of Verapamil hydrochloride release from compressed hydrophilic Polyox-Wsr tablets." Int'l J Pharmaceutics (1999) 189:105-111.

Dittmer, D.K., et al., "Glue-Sniffing Neuropathies," Canadian Family Physician 39:1965-1971 (1993).

Donnelly, C.L., "ADHD Medications: Past and Future," Behavioral Health Management, May/Jun. 2002, 28 & 30.

Dow, "Material Safety Data Sheet: Polyox(TM) WSR 30" (effective date: Sep. 18, 2001).

Dow, "Polyox Water-Soluble Resins: Degradation of Water-Soluble Resins," Technical Data (Oct. 2002).

Drug Bank "Oxymorphone," 2015; online, available at: www.dmgbank.ca/chugs/db01192 printed Jul. 1, 2015.

*Endo Pharmaceuticals Inc.* v. *Teva Pharmaceuticals USA, Inc.* (S.D.N.Y 2015)—Redacted Version.

FDA News Release, "FDA approves abuse-deterrent labeling for reformulated OxyContin," Apr. 16, 2013, available at http://www.fda.gov/NewsEvents/Newsroom/Press.Announcements/ucm348252.htm.

FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.

Final Draft Labeling for Concerta Extended-Release Tablets Attachment to Approval Letter (2000); available at: http://www.accessdata.fda.gov/drugsatfda_docs/label/2000/21121lbl.pdf.

Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).

Griffith, D., "Potential new ADHD drug creating lots of big hopes," Sacramento Bee (California), Oct. 30, 2002.

Huang, H. et al., "Preparation of Controlled Release Oral Dosage Forms by Low Temperature Melt Extrusion," AAPS PharmSci. 2000 2(S1).

Jaffe, S.L., "Failed Attempts at Intranasal Abuse of Concerta," Letters to the Editor, J. Am. Acad. Child Adolesc. Psychiatry, 41:1 (Jan. 2002).

Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.

Joint Claim Construction and Prehearing Statement, dated Jul. 11, 2014. *Janssen Pharmaceuticals, Inc. and Grünenthal GMBH* v. *Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH* v. *Roxane Laboratories, Inc.*, Civil Action No. 2:13-cv-06929 CCC-MF (D.N.J.), and *Janssen Pharmaceuticals, Inc. and Grünenthal GMBH* v. *Alkem Laboratories Limited*, Civil Action No. 2:13-cv-07803 CCC-MF (D.N.J.).

Kibbe, Coloring Agents, in Handbook of Pharmaceutical Excipients (3d ed. 2000).

Kidokoro, M. et al., "Properties of Tablets Containing Granulations of Ibuprofen and Acrylic Copolymers Prepared by Thermal Processes," Pharm Dev. and Tech. , 6:263-275 (2001).

Kinjo, N. et al, "Antiplasticization in the Slightly Plasticized Poly(vinyl chloride)," Polymer Journal 4(2):143-153 (1973).

Larhib, H. et al., "Compressing polyethyelene glycols: the effect of compression pressure and speed," Int 'l J Pharmaceutics (1997) 147: 199-205.

Lieberman, H., et al., Pharmaceutical Dosage Forms: Tablets, vol. 2, Ch. 5: Granulation Technology and Tablet Characterization (1990), Table of contents and 245-348.

Lyons et al., "Twitch Interpolation in the Assessment of the Maximum Force-Generating Capacity of the Jaw-Closing Muscles in Man," Arch. Oral. Biol. 41:12, 1161-1168 (1996).

Makki, A, et. Al., Eds., A Dictionary of American Idioms, 4th Ed. Barron's, New York (2004), 342-343.

Markovitz, H., et al. "Calculations of Entanglement Coupling Spacings in Linear Polymers." Journal of Physical Chemistry, 1962. 66(8): 1567-1568.

McCrum, N., et al., Principles of Polymer Engineering, 2nd ed., New York: Oxford University Press. 447(1997), Chapter 7, 296-351.

McGinity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.

McQuay, H. et a. "Methods of Therapeutic Trials," Textbook of Pain 1125-1138 (P.D. Wall & R. Melzack eds., Elsevier 4th ed. 1999), Table of Contents and 1125-1138.

Miura et al., "Comparison of Maximum Bite Force and Dentate Status Between Healthy and Frail Elderly Persons," J. Oral Rehabilitation, vol. 28 (2001), pp. 592-595.

Miyagawa, Y. et al., "Controlled-release of diclofenac sodium from wax matrix granulate," Int 'l J. Pharmaceutics (1996) 138:215-224.

National Drug Intelligence Center Information Bulletin "OxyContin Diversion and Abuse" Jan. 2001.

Payne, H. et al., Denatonium Benzoate as a Bitter Aversive Additive in Ethylene Glycol and Methanol-Based Automotive Products, SAE Technical Paper 930589, Abstract (1993).

Pilpel, N., et al. "The effect of temperature on the tensile strength and disintegration of paracetamol and oxytetracylcine tablets," J Pharm Pharmac., 29:389-392 (1977).

Polyox Water-Soluble Resins NF in Pharmaceutical Applications, Dow Chemical Company, Aug. 2002.

Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxycontin_msds.pdf.

Rauwendaal, Chris, PHD, Responsive Expert Report of Chris Rauwendaal, Ph.D. Regarding Expert Report of Michael M. Crowley, Ph.D., dated Jul. 17, 2015.

Repka, M. et al. Pharmaceutical Applications of Hot-Melt Extrusion: Part II. Drug Dev. & Indus. Pharmacy (2007) 33:1043-1057.

Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.

Seitz, J.A.; et al., "Evaluation of the Physical Properties of Compressed Tablets 1: Tablet Hardness and Friability," J. of Pharm. Sci. , 54:1353-1357 (1965).

Shah, et al., "Some Effects of Humidity and Heat on the Tableting Properties of Microcrystalline Cellulose Formulations 1," J. of Pharm. Sci., 57:181-182 (1967).

Singhal, et al., Handbook of Indices of Food Quality and Authenticity (1997), "Capsicum" p. 398-299.

Smith, K.L. et al. "High Molecular Weight Polymers of Ethylene Oxide—Plastic Properties." Industrial and Engineering Chemistiy, 1958. 50(1): 12-16.

Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.

Tiwari, D., et al., "Evaluation of polyoxyethylene homopolymers for buccal bioadhesive drug delivery device formulations." AAPS Pharmsci, 1999. 1(3): Article 13.

Wilkins, J.N., "Pharmacotherapy of Schizophrenia Patients with Comorbid Substance Abuse," Schizophrenia Bulletin, 23:215-228 (1997).

World Health Org., Cancer Pain Relief With a Guide to Opioid Availability (2d ed. 1996).

(56) References Cited

OTHER PUBLICATIONS

Yin, T.P., et al., "Viscoelastic Properties of Polyethylene Oxide in Rubber-Like State." Journal of Physical Chemistry, 1961. 65(3): 534-538.

Zacny, J. et al. Drug & Alcohol Dependence (2003) 69:215-232.

Zhang, F., "Hot-Melt Extrusion as a Novel Technology to Prepare Sustained-Release Dosage Forms," Dissertation University of Texas at Austin, Dec. 1999.

Extended European Search Report for Application No. EP 16183922.0-1460, dated Oct. 31, 2016.

Fathima, N. et al. "Drug-excipient interaction and its importance in dosage form development," Journal of Applied Pharmaceutical Science 01 (06); 2011, pp. 66-71.

Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.

Schilling, et al., "Novel application of hot-melt extrusion for the preparation of monolithic matrices containing enteric-coated particles." International Journal of Pharmaceutics 400 (2010) 34-31.

Starch 1500, Partially Pregelatinized Maize Starch, technical data from Colorcon, Feb. 2016, 6 pages.

Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.

COMPAP 90 technical data sheet Mar. 2014; 1 page.

Extended European Search Report for Application No. EP 16182124.4-1455, dated Jan. 17, 2017.

Furu et al. "Use of ADHD drugs in the Nordic countries: a population-based comparison study," Acta Psychiatrica Scandinavia, May 2010.

M. Xu et al., "Evaluation of the coat quality of sustained release pellets by individual pellet dissolution methodology," Int. J. Pharm. 478 (2015) 318-327.

PCT International Search Report and Written Opinion for PCT Application No. PCT/EP2017/070396 dated Sep. 8, 2017.

USP Expert Council, US Pharmacopoeia, Chapter 1092, 2007, 1-15.

Alekseeva et al, Chemical-Pharmaceutical Journal, vol. 41, No. 9, 2007, 49-52. (Full translation attached.).

Bannwarth, Bernard, "Will Abuse-Deterrent Formulations of Opioid Analgesics be Successful in Achieving Their Purpose?", Drugs, 2012, vol. 72, pp. 1713-1723.

\* cited by examiner

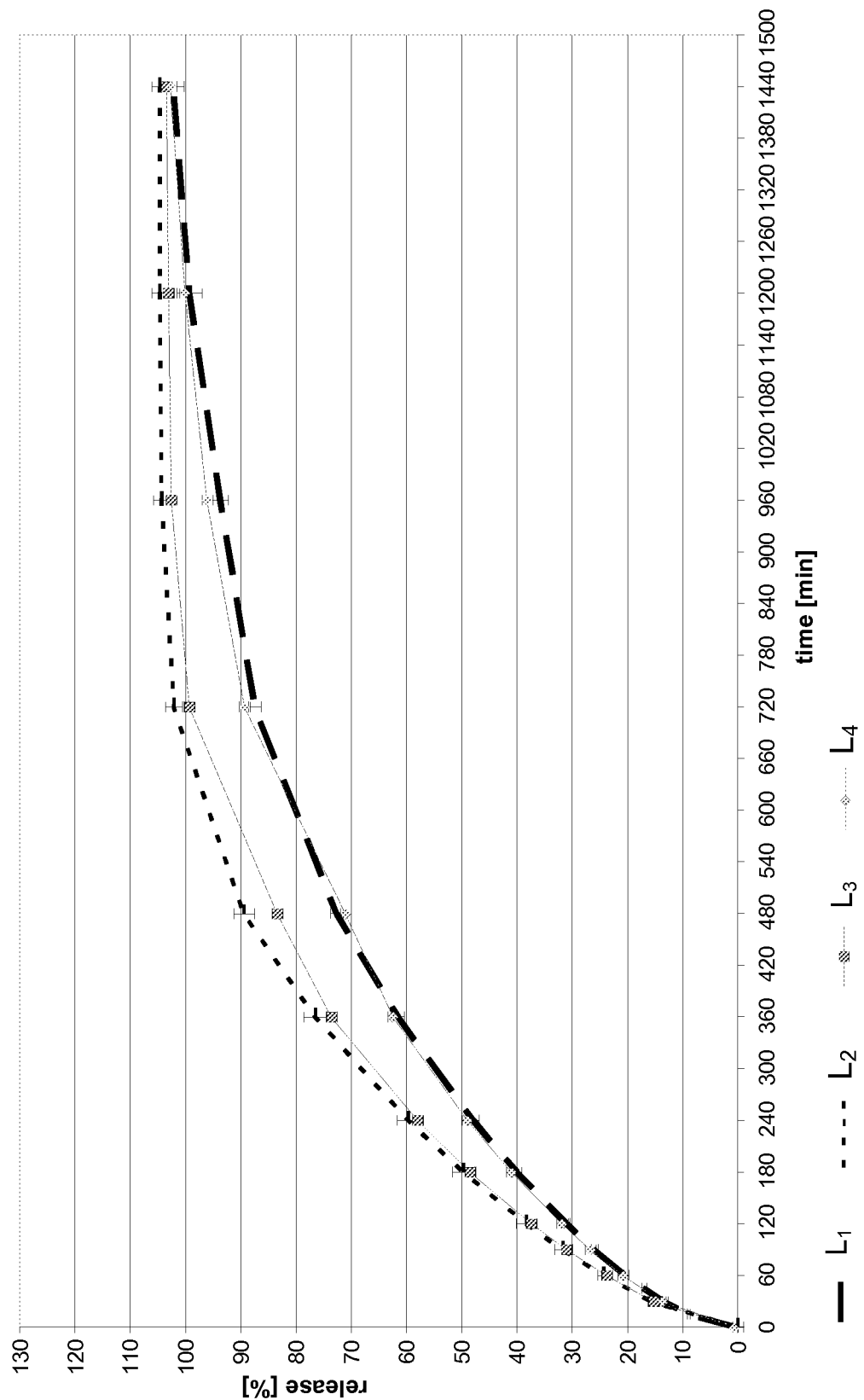

OXIDATION-STABILIZED TAMPER-RESISTANT DOSAGE FORM

This application is a continuation of U.S. patent application Ser. No. 14/192,916, filed Feb. 28, 2014, pending, which is a continuation of U.S. patent application Ser. No. 13/343,846, filed Jan. 5, 2012, abandoned, which is, in turn, a continuation of International Patent Application No. PCT/EP2010/004461, filed Jul. 21, 2010, which claims priority of European Patent Application No. 09009480.6, filed Jul. 22, 2009, the contents of both of which applications are incorporated herein by reference.

The invention relates to a pharmaceutical dosage form which is stabilized towards oxidation.

Many pharmacologically active compounds have a potential of being abused and thus, are advantageously provided in form of tamper resistant pharmaceutical dosage forms. Prominent examples of such pharmacologically active compounds are opioids.

It is known that abusers crush conventional tablets, which contain opioids, to defeat the time-release "micro-encapsulation" and then ingest the resulting powder orally, intranasally, rectally, or by injection.

Various concepts for the avoidance of drug abuse have been developed. One concept relies on the mechanical properties of the pharmaceutical dosage forms, particularly an increased breaking strength (resistance to crushing). The major advantage of such pharmaceutical dosage forms is that comminuting, particularly pulverization, by conventional means, such as grinding in a mortar or fracturing by means of a hammer, is impossible or at least substantially impeded.

Such pharmaceutical dosage forms are useful for avoiding drug abuse of the pharmacologically active compound contained therein, as they may not be powdered by conventional means and thus, cannot be administered in powdered from, e.g. nasally. The mechanical properties, particularly the high breaking strength of these pharmaceutical dosage forms renders them tamper resistant. In the context of such tamper resistant pharmaceutical dosage forms it can be referred to, e.g., WO 2005/016313, WO 2005/016314, WO 2005/063214, WO 2005/102286, WO 2006/002883, WO 2006/002884, WO 2006/002886, WO 2006/082097, WO 2006/082099, and WO 2008/107149.

These tamper resistant pharmaceutical dosage forms contain a synthetic or natural polymer, most often a high molecular weight polyethylene oxide, as matrix material.

Polyethylene oxides, like other aliphatic ethers, can undergo autoxidation in presence of oxygen to form hydroperoxides (see for instance C. W. McGary Jr., J. Polymer Sci., 2003, 46, 51-57). Subsequent radical reactions of the resulting peroxides lead to chain scission. These natural aging processes are catalyzed by other oxidation agents and are further accelerated by UV light and/or elevated temperatures. The oxidative degradation process is highly dependent on the molecular weight. High molecular weight polyethylene oxides are especially prone to autoxidation processes and degrade more rapidly than lower molecular weight polyethylene oxides.

Also oxidative sensitive pharmacologically active ingredients, such as opioids like oxymorphone, hydromorphone, and oxycodone, are sensitive towards oxidative degradation and decomposition processes.

As a result of the degradation processes, the properties of a dosage form containing oxidatively degradable matrix material and/or oxidative sensitive pharmacologically active ingredients may seriously be affected. For example, loss of content of the pharmacologically active ingredient as well as discoloration, decreased mechanical strength and accelerated drug release due to shortened polymer chains are likely to occur. Especially the breaking strength is highly dependent on the molecular weight of the polyalkylene oxide contained in the dosage form and thus directly influenced by chain scission processes.

Oxidation may be caused by molecular oxygen or by radicals or peroxides generated by compounds that come into close proximity with these oxidation-sensitive matrix materials and/or pharmacologically active ingredients.

Pharmaceutical excipients as such, e.g. polyethylene glycols, may cause or catalyze oxidative degradation, for example in the course of the process for manufacturing the pharmaceutical dosage forms. Further, molecular oxygen may generate said radicals or peroxides.

Typically, decomposition is monitored in standard storage stability tests e.g. under accelerated storage conditions, such as 40° C./75% rel. humidity. Under these conditions, degradation and decomposition typically proceeds faster than under ambient conditions. The drug approving authorities, such as CHMP and FDA, and international harmonization unions, such as ICH, have set standard storage stability thresholds which have to be met in order to get a pharmaceutical dosage form approved.

Particular problems arise when such pharmaceutical dosage forms comprising oxidative degradable matrix materials and/or oxidation-sensitive pharmacologically active ingredients need to be exposed to elevated temperatures in the course of the manufacturing process, such as hot-melt extrusion, film coating and the like. Under these conditions said compounds are even more sensitive towards oxidation. For example, several known processes for the manufacture of pharmaceutical dosage forms having an increased breaking strength require that a pharmaceutical composition containing the pharmacologically active ingredient is subjected to a specific amount of pressure at a specific elevated temperature for a specific period of time. Depending on the constituents of the pharmaceutical composition and their amounts, temperature, pressure and time may be varied within certain limits. However, if the minimal requirements are not satisfied, the breaking strength of the resultant pharmaceutical dosage form is too low.

In consequence, some conventional processes for the manufacture of pharmaceutical dosage forms, particularly for pharmaceutical dosage forms having an increased breaking strength, require comparatively harsh process conditions and thus, are so far not applicable for oxidation-sensitive matrix materials and/or pharmacologically active ingredients, e. g. opioids. In particular, chain rupture of pharmaceutical excipients such as polyethylene oxide during hot melt extrusion risks the formation of free radicals thereby further increasing the oxidative stress.

Lower dosages of oxidation-sensitive pharmacologically active ingredients often show a higher percentage of oxidative degradation and decomposition than higher dosages. Thus, as far as storage stability is concerned, pharmaceutical dosage forms containing lower dosages of oxidation-sensitive pharmacologically active ingredients need particular attention.

The effect of oxidation mechanisms and chemical interactions on stability of polymeric systems for amorphous $\Delta^9$-tetrahydrocannabinol (a non-opioid) produced by a hot-melt method is described in M. Munjal et al., J. Pharm. Sciences, 95(11), 2006, 2473-85. The study demonstrated for this highly unstable drug a complex nature of interactions including drug-excipient compatibility, use of antioxidants, cross-linking in polymeric matrixes, micro environment pH, and moisture effect.

K. C. Waterman et al., Pharm. Develop. Tech. 7(1), 2002, 1-32 reviews the stabilization of pharmaceuticals to oxidative degradation. Various methods for reducing oxidation are recommended. The authors conclude that in the end, every drug presents a unique situation.

WO 2008/107149 discloses oral dosage forms having an increased breaking strength that may contain redox stabilizers such as complexing agents, e.g. EDTA.

WO 2008/086804 relates to controlled release compositions containing a matrix composition comprising a) polymer or a mixture of polymers, b) an active drug substance and optionally c) one or more pharmaceutically acceptable excipients that is without alcohol induced dose dumping and have excellent properties with respect to avoiding drug abuse. Preferably, the composition is resistant to isolate and/or dissolve the active drug substance from the composition by crushing, melting and/or ethanol extraction, whereby the composition is resistant to drug abuse. Citric acid may be present as flavouring agent. Example 2 relates to a composition containing 7 wt.-% of citric acid.

WO 2008/148798 discloses an layered extended release composition for prolonged effect and a way to ensure prolonged effect e.g. once daily administration is to ensure optimal absorption of the active substance though the gastrointestinal tract i.e. from the stomach to rectum.

There is no general concept to successfully suppress oxidative degradation of oxidative degradable matrix materials such as polyethylene oxide and oxidation-sensitive drugs in pharmaceutical dosage forms. The complex individual oxidation mechanisms that are relevant for a particular matrix material or drug as well as the plurality of possible factors that have an influence on oxidation processes require extensive investigations in each particular case taking into account the particular circumstances. Possible methods to defend a dosage form from oxidative degradation processes are the addition of antioxidants, storage under an inert atmosphere or the application of an oxygen barrier film coating. The latter two methods are, however, difficult to apply during all stages of the manufacturing process.

It is further known that the oxidative degradation processes are especially accelerated when the dosage forms are exposed to harsh process conditions, e. g. during the manufacturing process. For example, high molecular weight polyethylene oxide tends to degrade upon hot-melt extrusion. Polymer degradation, however, may result in an uncontrolled release profile, particularly when the active ingredient is embedded in a matrix of the polyethylene oxide, and this might be another cause for oxidative degradation of the pharmacologically active ingredient by radicals. When adding suitable excipients in order to stabilize the high molecular weight polyethylene oxide, such as α-tocopherol, it should be taken into considerations that said excipients in turn may have a detrimental effect on the stability of other ingredients of the pharmaceutical dosage, e.g. of the pharmacologically active compound.

It is an object of the present invention to provide tamper-resistant pharmaceutical dosage forms containing pharmacologically active ingredients, particularly oxidation-sensitive opioids, that have advantages over the pharmaceutical dosage forms of the prior art. The pharmaceutical dosage forms should have improved storage stability, so that they may contain oxidation-sensitive opioids even at comparatively low doses. Further, it should be possible to prepare the pharmaceutical dosage forms by conventional processes under conventional conditions such as elevated temperature and pressure (e.g. in the course of thermoforming by hot-melt extrusion).

This object has been solved by the subject-matter of the patent claims.

The invention relates to a thermoformed pharmaceutical dosage form having a breaking strength of at least 300 N and comprising
- a pharmacologically active ingredient (A),
- a free physiologically acceptable acid (B) in an amount of from 0.001 to 5.0 wt.-%, based on the total weight of the pharmaceutical dosage form, and
- a polyalkylene oxide (C) having a weight average molecular weight $M_w$ of at least 200,000 g/mol.

It has been surprisingly found that pharmaceutical dosage forms containing oxidatively degradable polymers such as high molecular weight polyethylene oxide can be prevented from oxidative degradation and decomposition processes by the presence of suitable amounts of acid (B) in the pharmaceutical dosage forms according to the invention. By means of this method, it has been surprisingly found, that the specific material properties of the dosage form according to the invention such as the breaking strength and the retarded release of the active ingredient may be retained for a longer storage period.

Thus, the increased storage stability of the polymer matrix is reflected by an improved stability of the in vitro release profile upon storage and/or by an improved stability of the mechanical properties of the dosage forms. Both properties essentially rely upon the polymer matrix material.

It has further been surprisingly found that certain morphinan derivatives such as oxymorphone are oxidatively degraded to N-oxides (e.g., oxymorphone-N-oxide, N-oxides in general are often said to be toxic and possibly cancerogenic) upon manufacture and storage of the corresponding dosage forms and that the formation of said N-oxides and other decomposition products can be suppressed by the presence of suitable amounts of acid (B) in the pharmaceutical dosage forms according to the invention.

Thus, the increased storage stability of the pharmacologically active ingredient (A) is reflected by a decrease of impurities, if any, and a reduced decrease of the pharmacologically active ingredient (A) upon storage, if any, respectively.

While it is not intended to be bound to any theory, acid (B) seems to influence the micro-pH value of the pharmaceutical formulation thereby somehow increasing its storage stability. Thus, as far as the storage stability of the pharmacologically active ingredient is concerned, the stabilizing effect of acid (B) might correlate with the $pK_A$-value of the oxidation-sensitive drug. For example the $pK_A$-value of oxymorphone is 8.3. Conventional formulations of oxymorphone, which are tamper resistant due to their increased breaking strength but which do not show the desired shelf life, give a pH value of about 7.5 when being dispersed in water. Under these conditions, a considerable amount of the oxymorphone is present as a free base (i.e., is not protonated), which might be more sensitive towards oxidation than the (protonated) salt form.

This concept is further supported by the fact that in the absence of acid (B), the dosage forms tend to have a yellowish, beige color, while the presence of acid (B) leads to whiter, e.g. colorless tablets. Thus, the presence of acid (B) might decrease the pH value within the dosage form thereby improving drug and/or polymer resistance towards oxidative degradation.

It appears that the acidic nature of acid (B) is responsible for its stabilizing effect but not any other properties. This concept is supported by the fact that inorganic as well as organic acids both enhance the storage stability of the dosage form.

It has been surprisingly found that pharmaceutical excipients which are conventionally used in order to improve drug resistance towards oxidative degradation, particularly certain antioxidants, e.g., α-tocopherol, can be contra-productive and rather deteriorate than improve drug resistance towards oxidative degradation.

BRIEF DESCRIPTION OF THE DRAWING

FIG. 1 shows the in vitro release profile of pharmaceutical dosage forms according to inventive examples $L_1$ and $L_3$ and comparative examples $L_2$ and $L_4$.

The pharmaceutical dosage form according to the invention is thermoformed, preferably by extrusion, although also other methods of thermoforming may be used in order to manufacture the pharmaceutical dosage form according to the invention such as press-molding at elevated temperature or heating of tablets that were manufactured by conventional compression in a first step and then heated above the softening temperature of the polymer in the tablet in a second step to form hard tablets. In this regards, thermoforming means the forming or molding of a mass after the application of heat. In a preferred embodiment, the pharmaceutical dosage form is thermoformed by hot-melt extrusion.

Preferably, the pharmaceutical dosage form is a monolithic mass. The pharmaceutical dosage form is preferably prepared by hot-melt extrusion. The melt extruded strands are preferably cut into monoliths, which are then preferably formed into tablets. In this regard, the term "tablets" is preferably not to be understood as dosage forms being made by compression of powder or granules (compressi) but rather, as shaped extrudates.

The pharmaceutical dosage form according to the invention contains, as component (A), a pharmacologically active ingredient (A), preferably an oxidation-sensitive pharmacologically active ingredient. For the purpose of the specification, the term pharmacologically active ingredient (A) also includes the free base and the physiologically acceptable salts thereof.

For the purpose of the specification, the term oxidation-sensitive pharmacologically active ingredient includes all pharmacologically active ingredients that contain one or more functional group which is oxidized during the oxidative degradation process. Functional groups whose oxidation may cause a pharmacologically active ingredient to be instable towards oxidation, are double bonds, as well as aldehyde, keto, hydroxyl groups, ether, endiol, phenol and amino groups.

The dosage form according to the invention particularly preferably contains one or more pharmacologically active ingredients (A) selected from the group consisting of
- agents for the treatment and prevention of diseases of the alimentary system and metabolism [A]; in particular stomatological preparations [A01], agents for the treatment and prevention of acid-related disorders [A02], agents for the treatment and prevention of functional gastrointestinal tract disorders [A03], serotonin 5HT3 antagonists [A04AA], antihistamine preparations [A04AB], agents for bile and liver therapy [A05], laxatives [A06], intestinal antiinfectives [A07A], intestinal adsorbents [A07B], electrolytes with carbohydrates [A07C], intestinal antiinflammatory agents [A07E], microbial antidiarrhoeals [A07F], digestives including enzymes [A09], drugs used in diabetes [A10], vitamins [A11], minerals [A12], anabolic agents for systemic applications [A14] and appetite stimulants [A15];
- agents for the treatment and prevention of diseases of the blood and the blood forming organs [B]; in particular antithrombotic agents [B01], antihaemorrhagics [B02], antianaemic preparations [B03] and other haematological agents [B06];
- agents for the treatment and prevention of diseases of the cardiovascular system [C]; in particular agents for cardiac therapy [C01], antihypertensives [C02], diuretics [C03], peripheral vasodilatators [C04], vasoprotectives [C05], antihypotensives [C06A], β-adrenoceptor antagonists [C07], calcium channel blockers [C08], agents acting on the renin-angiotensin system [C09] and lipid reducing agents [C10];
- dermatologicals [D]; in particular antifungals for systemic use [D01B], antipsoriatics for systemic use [D05B], antiacne preparations for systemic use [D10B];
- agents for the treatment and prevention of diseases of the genitourinary system and sex hormones [G]; in particular gynaecological antiinfectives and antiseptics [G01], oxytocics [G02A], sympathomimetic labour repressants [G02CA], prolactin inhibitors [G02CB], hormonal contraceptives for systemic use [G03] and urologicals [G04];
- systemic hormone preparations excluding sex hormones and insulins [H]; in particular pituitary and hypothalamic hormones and analogue [H01], corticosteroids for systemic use [H02], thyroid preparations [H03], pancreatic hormones [H04], and agents for regulating calcium homeostatis [H05];
- antiinfectives for systemic use [J]; in particular antibiotics for systemic use [J01], antimycotics for systemic use [J02], antimycobacterials [J04], antivirals for systemic use [J05], immune sera and immunoglobulins [J06], and vaccines [J07]);
- antineoplastic and immunomodulating agents [L] (in particular antineoplastistic agents [L01], agents for endocrine therapy [L02], immunostimulants [L03] and immunosuppressive agents [L04];
- agents for the treatment and prevention of diseases of the musculo-skeletal system [M]; in particular antiinflammatory and antirheumatic agents [M01], peripherally acting muscle relaxants [M03A], directly acting muscle relaxants [M03C], antigout preparations [M04] and agents for the treatment of bone diseases [M05];
- agents for the treatment and prevention of diseases of the nervous system [N]; in particular salicylic acid the derivatives thereof [N02BA], pyrazolones [N02BB], anilides [N02BE], ergot alkaloids [N02CA], corticosteroid derivatives [N02CB], selective serotonin-5HT1 agonists [N02CC], hydantoin derivatives [N03AB], oxazolidine derivatives [N03AC], succinimide derivatives [N03AD], carboxamide derivatives [N03AF], fatty acid derivatives [N03AG], antiparkinson drugs [N04]), antipsychotics [N05A], antidepressants [N06A], antidementia drugs [N06D], parasympathomimetics [N07A] and antivertigo preparations [N07C];
- antiparasitic products, insecticides and repellents [P]; in particular antiprotozoals [P01], anthelmintics [P02] and ectoparasiticides, including scabicides, insecticides and repellents [P03];
- agents for the treatment and prevention of diseases of the respiratory system [R]; in particular nasal preparations

[R01], throat preparations [R02], drugs for obstructive airways diseases [R03], expectorants, excluding combinations with cough suppressants [R05C] and antihistamines for systemic use [R06];

agents for the treatment and prevention of diseases of the sensory organs [S]; in particular otologicals [S02]; and general diet products [V06] and therapeutic radiopharmaceuticals [V10], wherein the abbreviations stated in square brackets here (and hereinafter) correspond to the ATC Index, as used by the WHO for classifying pharmaceutical substances (preferred version: 2010).

In a preferred embodiment, the dosage form according to the invention contains one or more pharmacologically active ingredients (A) selected from the group consisting of agents for cardiac therapy [C01], preferably selected from the group consisting of cardiac glycosides [C01A], antiarrhythmics, class i and iii [C01B], cardiac stimulants excl. cardiac glycosides [C01C], vasodilators used in cardiac diseases [C01D], and other cardiac preparations [C01E].

In another preferred embodiment, the dosage form according to the invention contains one or more pharmacologically active ingredients (A) selected from the group consisting of antihypertensives [C02], preferably selected from the group consisting of antiadrenergic agents, centrally acting [C02A], antiadrenergic agents, ganglion-blocking [C02B], antiadrenergic agents, peripherally acting [C02C], arteriolar smooth muscle, agents acting on [C02D], other antihypertensives [C02K], antihypertensives and diuretics in combination [C02l], and combinations of antihypertensives in atc-gr. C02 [C02N].

In still another preferred embodiment, the dosage form according to the invention contains one or more pharmacologically active ingredients (A) selected from the group consisting of diuretics [C03], preferably selected from the group consisting of low-ceiling diuretics, thiazides [C03A], low-ceiling diuretics, excl. thiazides [C03B], high-ceiling diuretics [C03C], potassium-sparing agents [C03D], diuretics and potassium-sparing agents in combination [C03E], and other diuretics [C03X].

In yet another preferred embodiment, the dosage form according to the invention contains one or more pharmacologically active ingredients (A) selected from the group consisting of peripheral vasodilatators [C04], preferably selected from the group consisting of peripheral vasodilators [C04A].

In another preferred embodiment, the dosage form according to the invention contains one or more pharmacologically active ingredients (A) selected from the group consisting of vasoprotectives [C05], preferably selected from the group consisting of agents for treatment of hemorrhoids and anal fissures for topical use [C05A], antivaricose therapy [C05B], and capillary stabilizing agents [C05C].

In still another preferred embodiment, the dosage form according to the invention contains one or more pharmacologically active ingredients (A) selected from the group consisting of anti hypotensives [C06A].

In yet another preferred embodiment, the dosage form according to the invention contains one or more pharmacologically active ingredients (A) selected from the group consisting of ☐☐adrenoceptor antagonists [C07], preferably selected from the group consisting of beta blocking agents [C07A], beta blocking agents and thiazides [C07B], beta blocking agents and other diuretics [C07C], beta blocking agents, thiazides and other diuretics [C07D], beta blocking agents and vasodilators [C07E], and beta blocking agents and other antihypertensives [C07F].

In another preferred embodiment, the dosage form according to the invention contains one or more pharmacologically active ingredients (A) selected from the group consisting of calcium channel blockers [C08], preferably selected from the group consisting of selective calcium channel blockers with mainly vascular effects [C08C], selective calcium channel blockers with direct cardiac effects [C08D], non-selective calcium channel blockers [C08E], and calcium channel blockers and diuretics [C08G].

In still another preferred embodiment, the dosage form according to the invention contains one or more pharmacologically active ingredients (A) selected from the group consisting of agents acting on the renin-angiotensin system [C09], preferably selected from the group consisting of ACE inhibitors, plain [C09A], ACE inhibitors, combinations [C09B], angiotensin ii antagonists, plain [C09C], angiotensin ii antagonists, combinations [C09D], and other agents acting on the renin-angiotensin system [C09X].

In yet another preferred embodiment, the dosage form according to the invention contains one or more pharmacologically active ingredients (A) selected from the group consisting of lipid reducing agents [c10], preferably selected from the group consisting of lipid modifying agents, plain [C10A], and lipid modifying agents, combinations [C10B].

In a preferred embodiment, the pharmacologically active ingredient (A) is an angiotensin converting enzyme (ACE) inhibitor, more preferably an ACE-inhibitor selected from the group consisting of benazepril, captopril, cilazapril, enalapril, fosinopril, imidapril, lisinopril, moexipril, perindopril, quinapril, ramipril, spirapril, trandolapril and zofenopril.

In another preferred embodiment, the pharmacologically active ingredient is an opioid, more preferably an oxidation-sensitive opioid, most preferably oxymorphone or oxycodone.

According to the ATC index, opioids are divided into natural opium alkaloids, phenylpiperidine derivatives, diphenylpropylamine derivatives, benzomorphan derivatives, oripavine derivatives, morphinan derivatives and others. Examples of natural opium alkaloids are morphine, opium, hydromorphone, nicomorphine, oxycodone, dihydrocodeine, diamorphine, papaveretum, and codeine. Further opioids (A) are, for example, ethylmorphine, hydrocodone, oxymorphone, and the physiologically acceptable derivatives thereof or compounds, preferably the salts and solvates thereof, preferably the hydrochlorides thereof, physiologically acceptable enantiomers, stereoisomers, diastereomers and racemates and the physiologically acceptable derivatives thereof, preferably ethers, esters or amides.

Further preferred opioids include N-(1-methyl-2-piperidinoethyl)-N-(2-pyridyl)propionamide, (1R,2R)-3-(3-dimethylamino-1-ethyl-2-methyl-propyl)phenol, (1R,2R,4S)-2-(dimethylamino)methyl-4-(p-fluorobenzyloxy)-1-(m-methoxyphenyl)cyclohexanol, (1R,2R)-3-(2-dimethylaminomethyl-cyclohexyl)phenol, (1S,2S)-3-(3-dimethylamino-1-ethyl-2-methyl-propyl)phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexane-1,3-diol, preferably as racemate, 3-(2-dimethylaminomethyl-1-hydroxy-cyclohexyl)phenyl 2-(4-isobutyl-phenyl)propionate, 3-(2-dimethylaminomethyl-1-hydroxy-cyclohexyl)phenyl 2-(6-methoxy-naphthalen-2-yl)propionate, 3-(2-dimethylaminomethyl-cyclohex-1-enyl)-phenyl 2-(4-isobutyl-phenyl)propionate, 3-(2-dimethylaminomethylcyclohex-1-enyl)-phenyl 2-(6-methoxy-naphthalen-2-yl) propionate, (RR—SS)-2-acetoxy-4-trifluoromethyl-benzoic acid 3-(2-dimethylaminomethyl-1-hydroxy-cyclohexyl)-phenyl ester, (RR—SS)-2-hydroxy-4-trifluoromethyl-benzoic acid 3-(2-dimethylaminomethyl-1-hydroxy-cyclohexyl)-phenyl ester, (RR—SS)-4-chloro-2-hydroxy-benzoic acid 3-(2-dimethylaminomethyl-1-hydroxy-cyclohexyl)-phenyl ester, (RR—SS)-2-hydroxy-4-methyl-benzoic acid 3-(2-dimethylaminomethyl-1-hydroxy-cyclohexyl)-phenyl ester, (RR—SS)-2-hydroxy-4-methoxy-benzoic acid 3-(2-dimethylaminomethyl-1-hydroxy-cyclohexyl)-phenyl ester, (RR—SS)-2-hydroxy-5-nitro-benzoic acid 3-(2-dimethylaminomethyl-1-hydroxy-cyclohexyl)-phenyl ester, (RR—SS)-2',4'-difluoro-3-hydroxy-biphenyl-4-carboxylic acid 3-(2-dimethylaminomethyl-1-hydroxy-cyclohexyl)-phenyl ester, 1,1-(3-dimethylamino-3-phenylpentamethylen)-6-fluor-1,3,4,9-tetrahydropyrano[3,4-b]indole, in particular its hemicitrate; 1,1-[3-di methylamino-3-(2-thienyl)pentamethylen]-1,3,4,9-tetrahydropyrano[3,4-b]indole, in particular its citrate; and 1,1-[3-dimethylamino-3-(2-thienyl)-pentamethylen]-1,3,4,9-tetrahydropyrano[3,4-b]-6-fluoro-indole, in particular its hemicitrate, and corresponding stereoisomeric compounds, in each case the corresponding derivatives thereof, physiologically acceptable enantiomers, stereoisomers, diastereomers and racemates and the physiologically acceptable derivatives thereof, e.g. ethers, esters or amides, and in each case the physiologically acceptable compounds thereof, in particular the salts thereof and solvates, e.g. hydrochlorides.

Preferred opioids are of general formula (I)

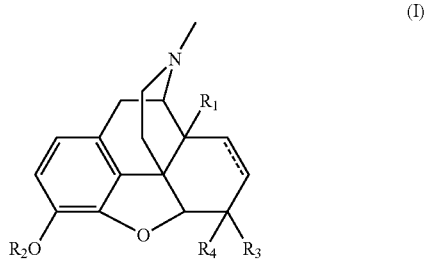

(I)

wherein
$R_1$ is —H, —OH or —$OC_{1-6}$-alkyl;
$R_2$ is —H or —$C_{1-6}$-alkyl;
$R_3$ is —H or —OH and $R_4$ is —H; or $R_3$ and $R_4$ together are =O; and
---- is an optional double bond;
or the physiologically acceptable salts thereof.

Particularly preferred opioids include oxymorphone, oxycodone, hydromorphone, and the physiologically acceptable salts thereof.

In another preferred embodiment, however, the pharmaceutical dosage form according to the invention does not contain any opioid, preferably any oxidation-sensitive opioid, as defined above.

The content of the pharmacologically active ingredient (A) in the pharmaceutical dosage form is not limited.

Preferably, its content is within the range of from 0.01 to 80 wt.-%, more preferably 0.1 to 50 wt.-%, still more preferably 1 to 25 wt.-%, based on the total weight of the pharmaceutical dosage form. In a preferred embodiment, the content of pharmacologically active ingredient (A) is within the range of from 7±6 wt.-%, more preferably 7±5 wt.-%, still more preferably 5±4 wt.-%, 7±4 wt.-% or 9±4 wt.-%, most preferably 5±3 wt.-%, 7±3 wt.-% or 9±3 wt.-%, and in particular 5±2 wt.-%, 7±2 wt.-% or 9±2 wt.-%, based on the total weight of the pharmaceutical dosage form. In another preferred embodiment, the content of pharmacologically active ingredient (A) is within the range of from 11±10 wt.-%, more preferably 11±9 wt.-%, still more preferably 9±6 wt.-%, 11±6 wt.-%, 13±6 wt.-% or 15±6 wt.-%, most preferably 11±4 wt.-%, 13±4 wt.-% or 15±4 wt.-%, and in particular 11±2 wt.-%, 13±2 wt.-% or 15±2 wt.-%, based on the total weight of the pharmaceutical dosage form. In a further preferred embodiment, the content of pharmacologically active ingredient (A) is within the range of from 20±6 wt.-%, more preferably 20±5 wt.-%, still more preferably 20±4 wt.-%, most preferably 20±3 wt.-%, and in particular 20±2 wt.-%, based on the total weight of the pharmaceutical dosage form.

Preferably, the total amount of the pharmacologically active ingredient (A) that is contained in the pharmaceutical dosage form is within the range of from 0.01 to 200 mg, more preferably 0.1 to 190 mg, still more preferably 1.0 to 180 mg, yet more preferably 1.5 to 160 mg, most preferably 2.0 to 100 mg and in particular 2.5 to 80 mg.

In a preferred embodiment, the pharmacologically active ingredient (A) is contained in the pharmaceutical dosage form in an amount of 7.5±5 mg, 10±5 mg, 20±5 mg, 30±5 mg, 40±5 mg, 50±5 mg, 60±5 mg, 70±5 mg, 80±5 mg, 90±5 mg, 100±5 mg, 110±5 mg, 120±5 mg, 130±5, 140±5 mg, 150±5 mg, or 160±5 mg. In another preferred embodiment, the pharmacologically active ingredient (A) is contained in the pharmaceutical dosage form in an amount of 5±2.5 mg, 7.5±2.5 mg, 10±2.5 mg, 15±2.5 mg, 20±2.5 mg, 25±2.5 mg, 30±2.5 mg, 35±2.5 mg, 40±2.5 mg, 45±2.5 mg, 50±2.5 mg, 55±2.5 mg, 60±2.5 mg, 65±2.5 mg, 70±2.5 mg, 75±2.5 mg, 80±2.5 mg, 85±2.5 mg, 90±2.5 mg, 95±2.5 mg, 100±2.5 mg, 105±2.5 mg, 110±2.5 mg, 115±2.5 mg, 120±2.5 mg, 125±2.5 mg, 130±2.5 mg, 135±2.5 mg, 140±2.5 mg, 145±2.5 mg, 150±2.5 mg, 155±2.5 mg, or 160±2.5 mg.

In a particularly preferred embodiment, the pharmacologically active ingredient (A), preferably the opioid, is oxymorphone, preferably its HCl salt, and the pharmaceutical dosage form is adapted for administration twice daily. In this embodiment, the opioid (A) is preferably contained in the pharmaceutical dosage form in an amount of from 5 to 40 mg. In another particularly preferred embodiment, pharmacologically active ingredient (A), preferably the opioid is oxymorphone, preferably its HCl, and the pharmaceutical dosage form is adapted for administration once daily. In this embodiment, pharmacologically active ingredient (A), preferably the opioid is preferably contained in the pharmaceutical dosage form in an amount of from 10 to 80 mg.

In another particularly preferred embodiment, the pharmacologically active ingredient (A), preferably the opioid, is oxycodone, preferably its HCl salt, and the pharmaceutical dosage form is adapted for administration twice daily. In this embodiment, the pharmacologically active ingredient (A), preferably the opioid, is preferably contained in the pharmaceutical dosage form in an amount of from 5 to 80 mg. In another particularly preferred embodiment, the pharmacologically active ingredient (A), preferably the opioid, is oxycodone, preferably its HCl salt, and the pharmaceutical dosage form is adapted for administration once daily. In this embodiment, the pharmacologically active ingredient (A), preferably the opioid, is preferably contained in the pharmaceutical dosage form in an amount of from 10 to 320 mg.

In still another particularly preferred embodiment, the pharmacologically active ingredient (A), preferably the opioid, is hydromorphone, preferably its HCl salt, and the pharmaceutical dosage form is adapted for administration twice daily. In this embodiment, the pharmacologically active ingredient (A), preferably the opioid, is preferably contained in the pharmaceutical dosage form in an amount of from 2 to 52 mg. In another particularly preferred embodiment, the pharmacologically active ingredient (A), preferably the opioid, is hydromorphone, preferably its HCl salt, and the pharmaceutical dosage form is adapted for administration once daily. In this embodiment, the pharmacologically active ingredient (A), preferably the opioid, is preferably contained in the pharmaceutical dosage form in an amount of from 4 to 104 mg.

The pharmaceutical dosage form according to the invention is characterized by excellent storage stability.

Preferably, after storage for 4 weeks at 40° C. and 75% rel. humidity, the content of the pharmacologically active ingredient (A), preferably the opioid, amounts to at least 98.0%, more preferably at least 98.5%, still more preferably at least 99.0%, yet more preferably at least 99.2%, most preferably at least 99.4% and in particular at least 99.6%, of its original content before storage. Suitable methods for measuring the content of the pharmacologically active ingredient (A) in the pharmaceutical dosage form are known to the skilled artisan. In this regard it is referred to the Eur. Ph. or the USP, especially to reversed phase HPLC analysis. Preferably, the pharmaceutical dosage form is stored in closed, preferably sealed containers, preferably as described in the experimental section, most preferably being equipped with an oxygen scavenger, in particular with an oxygen scavenger that is effective even at low relative humidity.

Preferably, after storage for 4 weeks at 40° C. and 75% rel. humidity, the content of the matrix material, preferably the polyalkylene oxide (C) amounts to at least 98.0%, more preferably at least 98.5%, still more preferably at least 99.0%, yet more preferably at least 99.2%, most preferably at least 99.4% and in particular at least 99.6%, of its original content before storage. Suitable methods for measuring the content of the polyalkylene oxide (C) in the pharmaceutical dosage form are known to the skilled artisan. In this regard it is referred to the Eur. Ph. or the USP, especially to reversed phase HPLC analysis.

Preferably, after storage for 4 weeks at 40° C. and 75% rel. humidity, the weight average molecular weight of the polyalkylene oxide (C) amounts to at least 70%, more preferably at least 75%, still more preferably at least 80%, yet more preferably at least 85%, most preferably at least 90% and in particular at least 95%, of its original weight average molecular weight before storage.

Suitable methods for determining the weight average molecular weight of the polyalkylene oxide (C) in the pharmaceutical dosage form are known to the skilled artisan. The change of the weight average molecular weight of the polyalkylene oxide (C) can for instance be evaluated by viscosity measurements after swelling of the dosage form.

It has been surprisingly found that acid (B) does not only improve the storage stability of the dosage form but also improves the processability of the pharmaceutical excipients, preferably of the polyalkylene oxide (C) upon manufacture, particularly in the course of thermoforming such as hot-melt extrusion. There is comparative experimental evidence that due to the presence of acid (B) the decrease of viscosity of polymer (C) which typically occurs upon hot-melt extrusion is substantially reduced when acid (B) is present in suitable amounts.

Preferably, the dosage form according to the invention contains acid (B) in an amount so that in the course of hot-melt extrusion of all excipients and ingredients the gel viscosity of a homogeneous gel prepared from the dosage form amounts to at least 50%, more preferably at least 60%, still more preferably at least 70%, yet more preferably at least 80%, even more preferably at least 85%, most preferably at least 90% and in particular at least 95% of the gel viscosity of a homogeneous gel prepared from a mixture of all excipients and ingredients of the dosage form but which has not been hot-melt extruded.

Furthermore, the dosage form according to the invention preferably contains acid (B) in an amount so that after storage of the dosage form for 3 months under accelerated storage conditions the gel viscosity of a homogeneous gel prepared from the dosage form amounts to at least 50%, more preferably at least 60%, still more preferably at least 70%, yet more preferably at least 80%, even more preferably at least 85%, most preferably at least 90% and in particular at least 95% of the gel viscosity of a homogeneous gel prepared from the dosage form prior to storage. Preferably, the conditions of extrusion are defined as in the experimental section. When preparing the homogeneous gel, the dosage form is preferably suspended in a sufficient amount of water so that at ambient conditions (rotational viscosimeter) the viscosity of the resultant homogeneous gel is about 500 mPas at 40 s$^{-1}$ (linearity range). Once a suitable amount of water has been determined by preliminary tests, all comparative tests are then conducted under identical conditions.

Preferably, the pharmaceutical dosage form is stored in closed, preferably sealed containers, preferably as described in the experimental section, most preferably being equipped with an oxygen scavenger, in particular with an oxygen scavenger that is effective even at low relative humidity.

The pharmaceutical dosage form according to the invention contains, as component (B), a free physiologically acceptable acid in an amount of from 0.001 to 5.0 wt.-%, based on the total weight of the pharmaceutical dosage form.

The acid (B) may be organic or inorganic, liquid or solid. Solid acids are preferred, particularly crystalline organic or inorganic acids.

Acid (B) is free. This means that the acidic functional groups of the acid (B) are not all together constituents of a salt of the pharmacologically active ingredient (A). If the pharmacologically active ingredient (A) is present as a salt of an acid, e.g. as hydrochloride, the pharmaceutical dosage form according to the invention preferably contains as component (B) another, chemically different acid which is not present as a constituent of the salt of the pharmacologically active ingredient (A). In other words, monoacids that form a salt with pharmacologically active ingredient (A) are not to be considered as free acids (B) in the meaning of the present invention. When acid (B) has more than a single acidic functional group (e.g. phosphoric acid), the acid (B) may be present as a constituent of a salt of the pharmacologically active ingredient (A), provided that at least one of the acidic functional groups of the acid (B) is not involved in the formation of the salt, i.e. is free. Preferably, however, each and every acidic functional group of acid (B) is not involved in the formation of a salt with pharmacologically active ingredient (A). It is also possible, however, that free acid (B) and the acid forming a salt with pharmacologically active ingredient (A) are identical. Under these circumstances the acid is preferably present in molar excess compared to pharmacologically active ingredient (A).

In a preferred embodiment, the acid (B) contains at least one acidic functional group (e.g. —$CO_2H$, —$SO_3H$, —$PO_3H_2$, —OH and the like) having a p$K_A$ value within the range of 2.00±1.50, more preferably 2.00±1.25, still more preferably 2.00±1.00, yet more preferably 2.00±0.75, most preferably 2.00±0.50 and in particular 2.00±0.25. In another preferred embodiment, the acid contains at least one acidic functional group having a $pK_A$ value within the range of 2.25±1.50, more preferably 2.25±1.25, still more preferably 2.25±1.00, yet more preferably 2.25±0.75, most preferably 2.25±0.50 and in particular 2.25±0.25. In another preferred embodiment, the acid (B) contains at least one acidic functional group having a $pK_A$ value within the range of 2.50±1.50, more preferably 2.50±1.25, still more preferably 2.50±1.00, yet more preferably 2.50±0.75, most preferably 2.50±0.50 and in particular 2.50±0.25. In another preferred embodiment, the acid (B) contains at least one acidic functional group having a $pK_A$ value within the range of 2.75±1.50, more preferably 2.75±1.25, still more preferably 2.75±1.00, yet more preferably 2.75±0.75, most preferably 2.75±0.50 and in particular 2.75±0.25. In another preferred embodiment, the acid (B) contains at least one acidic functional group having a $pK_A$ value within the range of 3.00±1.50, more preferably 3.00±1.25, still more preferably 3.00±1.00, yet more preferably 3.00±0.75, most preferably 3.00±0.50 and in particular 3.00±0.25. In still another preferred embodiment, the acid (B) contains at least one acidic functional group having a $pK_A$ value within the range of 3.25±1.50, more preferably 3.25±1.25, still more preferably 3.25±1.00, yet more preferably 3.25±0.75, most preferably 3.25±0.50 and in particular 3.25±0.25.

In yet another preferred embodiment, the acid (B) contains at least one acidic functional group having a $pK_A$ value within the range of 4.50±1.50, more preferably 4.50±1.25, still more preferably 4.50±1.00, yet more preferably 4.50±0.75, most preferably 4.50±0.50 and in particular 4.50±0.25. In yet another preferred embodiment, the acid (B) contains at least one acidic functional group having a $pK_A$ value within the range of 4.75±1.50, more preferably 4.75±1.25, still more preferably 4.75±1.00, yet more preferably 4.75±0.75, most preferably 4.75±0.50 and in particular 4.75±0.25. In yet another preferred embodiment, the acid (B) contains at least one acidic functional group having a $pK_A$ value within the range of 5.00±1.50, more preferably 5.00±1.25, still more preferably 5.00±1.00, yet more preferably 5.00±0.75, most preferably 5.00±0.50 and in particular 5.00±0.25.

Preferably, the acid (B) is an organic carboxylic or sulfonic acid, particularly a carboxylic acid. Multicarboxylic acids and/or hydroxy-carboxylic acids are especially preferred.

In case of multicarboxylic acids, the partial salts thereof are also to be regarded as multicarboxylic acids, e.g. the partial sodium, potassium or ammonium salts. For example, citric acid is a multicarboxylic acid having three carboxyl groups. As long as there remains at least one carboxyl group protonated (e.g. sodium dihydrogen citrate or disodium hydrogen citrate), the salt is to be regarded as a multicarboxylic acid. Preferably, however, all carboxyl groups of the multicarboxylic acid are protonated.

Preferably, the acid (B) is of low molecular weight, i.e., not polymerized. Typically, the molecular weight of the acid (B) is below 500 g/mol.

Examples of acids include saturated and unsaturated monocarboxylic acids, saturated and unsaturated bicarboxylic acids, tricarboxylic acids, α-hydroxyacids and β-hydroxyl-acids of monocarboxylic acids, α-hydroxyacids and β-hydroxyacids of bicarboxylic acids, α-hydroxyacids and β-hydroxyacids of tricarboxylic acids, ketoacids, α-ketoacids, β-ketoacids, of the polycarboxylic acids, of the polyhydroxy monocarboxylic acids, of the polyhydroxy bicarboxylic acids, of the polyhydroxy tricarboxylic acids.

Preferably, the acid (B) is selected from the group consisting of benzenesulfonic acid, citric acid, α-glucoheptonic acid, D-gluconic acid, glycolic acid, lactic acid, malic acid, malonic acid, mandelic acid, propanoic acid, succinic acid, tartaric acid (d, l, or dl), tosic acid (toluenesulfonic acid), valeric acid, palmitic acid, pamoic acid, sebacic acid, stearic acid, lauric acid, acetic acid, adipic acid, glutaric acid, 4-chlorobenzenesulfonic acid, ethanedisulfonic acid, ethylsuccinic acid, fumaric acid, galactaric acid (mucic acid), D-glucuronic acid, 2-oxo-glutaric acid, glycerophosphoric acid, hippuric acid, isethionic acid (ethanolsulfonic acid), lactobionic acid, maleic acid, maleinic acid, 1,5-naphthalene-disulfonic acid, 2-naphthalene-sulfonic acid, pivalic acid, terephthalic acid, thiocyanic acid, cholic acid, n-dodecyl sulfate, 3-hydroxy-2-naphthoic acid, 1-hydroxy-2-naphthoic acid, oleic acid, undecylenic acid, ascorbic acid, (+)-camphoric acid, d-camphorsulfonic acid, dichloroacetic acid, ethanesulfonic acid, formic acid, methanesulfonic acid, nicotinic acid, orotic acid, oxalic acid, picric acid, L-pyroglutamic acid, saccharine, salicylic acid, gentisic acid, and/or 4-acetamidobenzoic acid.

The content of the acid (B) is within the range of from 0.001 to 5.0 wt.-%, preferably 0.005 to 2.5 wt.-%, more preferably 0.01 to 2.0 wt.-%, still more preferably 0.05 to 1.5 wt.-%, most preferably 0.1 to 1.0 wt.-% and in particular 0.2 to 0.9 wt.-%, based on the total weight of the pharmaceutical dosage form.

Preferably, the acid (B) is a multicarboxylic acid. More preferably, the multicarboxylic acid is selected from the group consisting of citric acid, maleic acid and fumaric acid.

Citric acid is particularly preferred.

The multicarboxylic acid, preferably citric acid, may be present in its anhydrous form or as a solvate and hydrate, respectively, e.g., as monohydrate.

In a preferred embodiment, the content of the acid (B), preferably citric acid, is within the range of 0.2±0.18 wt.-%, more preferably 0.2±0.15 wt.-%, still more preferably 0.2±0.12 wt.-%, yet more preferably 0.2±0.09 wt.-%, most preferably 0.2±0.06 wt.-%, and in particular 0.2±0.03 wt.-%, based on the total weight of the pharmaceutical dosage form.

In another preferred embodiment, the content of the acid (B), preferably citric acid, is within the range of 0.3±0.18 wt.-%, more preferably 0.3±0.15 wt.-%, still more preferably 0.3±0.12 wt.-%, yet more preferably 0.3±0.09 wt.-%, most preferably 0.3±0.06 wt.-%, and in particular 0.3±0.03 wt.-%, based on the total weight of the pharmaceutical dosage form.

In still another preferred embodiment, the content of the acid (B), preferably citric acid, is within the range of 0.4±0.18 wt.-%, more preferably 0.4±0.15 wt.-%, still more preferably 0.4±0.12 wt.-%, yet more preferably 0.4±0.09 wt.-%, most preferably 0.4±0.06 wt.-%, and in particular 0.4±0.03 wt.-%, based on the total weight of the pharmaceutical dosage form.

In yet another preferred embodiment, the content of the acid (B), preferably citric acid, is within the range of 0.5±0.18 wt.-%, more preferably 0.5±0.15 wt.-%, still more preferably 0.5±0.12 wt.-%, yet more preferably 0.5±0.09 wt.-%, most preferably 0.5±0.06 wt.-%, and in particular 0.5±0.03 wt.-%, based on the total weight of the pharmaceutical dosage form.

In yet another preferred embodiment, the content of the acid (B), preferably citric acid, is within the range of 0.6±0.18 wt.-%, more preferably 0.6±0.15 wt.-%, still more preferably 0.6±0.12 wt.-%, yet more preferably 0.6±0.09 wt.-%, most preferably 0.6±0.06 wt.-%, and in particular 0.6±0.03 wt.-%, based on the total weight of the pharmaceutical dosage form.

In yet another preferred embodiment, the content of the acid (B), preferably citric acid, is within the range of 0.7±0.18 wt.-%, more preferably 0.7±0.15 wt.-%, still more preferably 0.7±0.12 wt.-%, yet more preferably 0.7±0.09 wt.-%, most preferably 0.7±0.06 wt.-%, and in particular 0.7±0.03 wt.-%, based on the total weight of the pharmaceutical dosage form.

In yet another preferred embodiment, the content of the acid (B), preferably citric acid, is within the range of 0.8±0.18 wt.-%, more preferably 0.8±0.15 wt.-%, still more preferably 0.8±0.12 wt.-%, yet more preferably 0.8±0.09 wt.-%, most preferably 0.8±0.06 wt.-%, and in particular 0.8±0.03 wt.-%, based on the total weight of the pharmaceutical dosage form.

In yet another preferred embodiment, the content of the acid (B), preferably citric acid, is within the range of 0.85±0.18 wt.-%, more preferably 0.85±0.15 wt.-%, still more preferably 0.85±0.12 wt.-%, yet more preferably 0.85±0.09 wt.-%, most preferably 0.85±0.06 wt.-%, and in particular 0.85±0.03 wt.-%, based on the total weight of the pharmaceutical dosage form.

In still another preferred embodiment, the content of the acid (B), preferably citric acid, is within the range of 0.9±0.18 wt.-%, more preferably 0.9±0.15 wt.-%, still more preferably 0.9±0.12 wt.-%, yet more preferably 0.9±0.09 wt.-%, most preferably 0.9±0.06 wt.-%, and in particular 0.9±0.03 wt.-%, based on the total weight of the pharmaceutical dosage form.

In a further preferred embodiment, the content of the acid (B), preferably citric acid, is within the range of 1.0±0.18 wt.-%, more preferably 1.0±0.15 wt.-%, still more preferably 1.0±0.12 wt.-%, yet more preferably 1.0±0.09 wt.-%, most preferably 1.0±0.06 wt.-%, and in particular 1.0±0.03 wt.-%, based on the total weight of the pharmaceutical dosage form.

The pharmaceutical dosage form according to the invention comprises, as component (C), a polyalkylene oxide (C) having a weight average molecular weight $M_w$ of at least 200,000 g/mol, preferably at least 500,000 g/mol, more preferably at least 750,000 g/mol, still more preferably at least 1,000,000 g/mol, most preferably at least 2,000,000 g/mol and in particular within the range of from 500,000 to Ser. No. 15/000,000 g/mol.

Preferably, the polyalkylene oxide is selected from the group consisting of polymethylene oxide, polyethylene oxide and polypropylene oxide, the copolymers and mixtures thereof.

Polyalkylene oxide (C) may comprise a single polyalkylene oxide having a particular average molecular weight, or a mixture (blend) of different polymers, such as two, three, four or five polymers, e.g., polymers of the same chemical nature but different average molecular weight, polymers of different chemical nature but same average molecular weight, or polymers of different chemical nature as well as different molecular weight.

For the purpose of the specification, a polyalkylene glycol has a molecular weight of up to 20,000 g/mol whereas a polyalkylene oxide has a molecular weight of more than 20,000 g/mol. In a preferred embodiment, the weight average over all molecular weights of all polyalkylene oxides that are contained in the pharmaceutical dosage form is at least 200,000 g/mol. Thus, polyalkylene glycols, if any, are preferably not taken into consideration when determining the weight average molecular weight of polyalkylene oxide (C).

Preferably, the content of the polyalkylene oxide (C) is within the range of from 20 to 99 wt.-%, more preferably 25 to 95 wt.-%, still more preferably 30 to 90 wt.-%, yet more preferably 30 to 85 wt.-%, most preferably 30 to 80 wt.-% and in particular 30 to 75 wt.-%, based on the total weight of the pharmaceutical dosage form. In a preferred embodiment, the content of the polyalkylene oxide is at least 20 wt.-%, more preferably at least 25 wt.-%, still more preferably at least 30 wt.-%, yet more preferably at least 35 wt.-% and in particular at least 40 wt.-%.

In a preferred embodiment, the overall content of polyalkylene oxide (C) is within the range of 25±20 wt.-%, more preferably 25±15 wt.-%, most preferably 25±10 wt.-%, and in particular 25±5 wt.-%. In another preferred embodiment, the overall content of polyalkylene oxide (C) is within the range of 35±20 wt.-%, more preferably 35±15 wt.-%, most preferably 35±10 wt.-%, and in particular 35±5 wt.-%. In still another preferred embodiment, the overall content of polyalkylene oxide (C) is within the range of 45±20 wt.-%, more preferably 45±15 wt.-%, most preferably 45±10 wt.-%, and in particular 45±5 wt.-%. In yet another preferred embodiment, the overall content of polyalkylene oxide (C) is within the range of 55±20 wt.-%, more preferably 55±15 wt.-%, most preferably 55±10 wt.-%, and in particular 55±5 wt.-%. In a further preferred embodiment, the overall content of polyalkylene oxide (C) is within the range of 65±20 wt.-%, more preferably 65±15 wt.-%, most preferably 65±10 wt.-%, and in particular 65±5 wt.-%. In still a further a preferred embodiment, the overall content of polyalkylene oxide (C) is within the range of 75±20 wt.-%, more preferably 75±15 wt.-%, most preferably 75±10 wt.-%, and in particular 75±5 wt.-%. In a still further a preferred embodiment, the overall content of polyalkylene oxide (C) is within the range of 80±15 wt.-%, more preferably 80±10 wt.-%, and most preferably 80±5 wt.-%.

In a preferred embodiment, polyalkylene oxide (C) is homogeneously distributed in the pharmaceutical dosage form according to the invention. Preferably, polyalkylene oxide (C) forms a matrix in which the opioid (A) is embedded. In a particularly preferred embodiment, the opioid (A) and polyalkylene oxide (C) are intimately homogeneously distributed in the pharmaceutical dosage form so that the pharmaceutical dosage form does not contain any segments where either opioid (A) is present in the absence of polyalkylene oxide (C) or where polyalkylene oxide (C) is present in the absence of opioid (A).

When the pharmaceutical dosage form is film coated, the polyalkylene oxide (C) is preferably homogeneously distributed in the core of the pharmaceutical dosage form, i.e. the film coating preferably does not contain polyalkylene oxide (C). Nonetheless, the film coating as such may of course contain one or more polymers, which however, preferably differ from the polyalkylene oxide (C) contained in the core.

The polyalkylene oxide (C) may be combined with one or more different polymers selected from the group consisting of polyalkylene oxide, preferably polymethylene oxide, polyethylene oxide, polypropylene oxide; polyethylene, polypropylene, polyvinyl chloride, polycarbonate, polystyrene, polyvinylpyrrolidone, poly(alk)acrylate, poly(hydroxy fatty acids), such as for example poly(3-hydroxybutyrate-co-3-hydroxyvalerate) (Biopol®), poly(hydroxyvaleric acid); polycaprolactone, polyvinyl alcohol, polyesteramide, polyethylene succinate, polylactone, polyglycolide, polyurethane, polyamide, polylactide, polyacetal (for example polysaccharides optionally with modified side chains), polylactide/glycolide, polylactone, polyglycolide, polyorthoester, polyanhydride, block polymers of polyethylene glycol and polybutylene terephthalate (Polyactive®), polyanhydride (Polifeprosan), copolymers thereof, block-copolymers thereof, and mixtures of at least two of the stated polymers, or other polymers with the above characteristics.

Preferably, the molecular weight dispersity $M_w/M_n$ of polyalkylene oxide (C) is within the range of 2.5±2.0, more preferably 2.5±1.5, still more preferably 2.5±1.0, yet more preferably 2.5±0.8, most preferably 2.5±0.6, and in particular 2.5±0.4.

The polyalkylene oxide (C) (starting material) preferably has a viscosity at 25° C. of 30 to 17,600 cP, more preferably 55 to 17,600 cP, still more preferably 600 to 17,600 cP and most preferably 4,500 to 17,600 cP, measured in a 5 wt.-% aqueous solution using a model RVF Brookfield viscosimeter (spindle no. 2/rotational speed 2 rpm); of 400 to 4,000 cP, more preferably 400 to 800 cP or 2,000 to 4,000 cP, measured on a 2 wt.-% aqueous solution using the stated viscosimeter (spindle no. 1 or 3/rotational speed 10 rpm); or of 1,650 to 10,000 cP, more preferably 1,650 to 5,500 cP, 5,500 to 7,500 cP or 7,500 to 10,000 cP, measured on a 1 wt.-% aqueous solution using the stated viscosimeter (spindle no. 2/rotational speed 2 rpm).

In a preferred embodiment according to the invention the polyalkylene oxide (C) having a weight average molecular weight of at least 200,000 g/mol is combined with at least one further polymer, preferably but not necessarily also having a weight average molecular weight ($M_w$) of at least 200,000 g/mol, selected from the group consisting of polyethylene, polypropylene, polyvinyl chloride, polycarbonate, polystyrene, polyacrylate, poly(hydroxy fatty acids), polycaprolactone, polyvinyl alcohol, polyesteramide, polyethylene succinate, polylactone, polyglycolide, polyurethane, polyvinylpyrrolidone, polyamide, polylactide, polylactide/glycolide, polylactone, polyglycolide, polyorthoester, polyanhydride, block polymers of polyethylene glycol and polybutylene terephthalate, polyanhydride, polyacetal, cellulose esters, cellulose ethers and copolymers thereof. Cellulose esters and cellulose ethers are particularly preferred, e.g. methylcellulose, ethylcellulose, hydroxymethylcellulose, hydroxyethylcellulose, hydroxypropylcellulose hydroxypropylmethylcellulose, carboxymethylcellulose, and the like.

In a preferred embodiment, said further polymer is neither a polyalkylene oxide nor a polyalkylene glycol. Nonetheless, the pharmaceutical dosage form may contain polyalkylene glycol, e.g. as plasticizer, but then, the pharmaceutical dosage form preferably is a ternary mixture of polymers: polyalkylene oxide (C)+further polymer+plasticizer.

In a particularly preferred embodiment, said further polymer is a hydrophilic cellulose ester or cellulose ether, preferably hydroxypropylmethylcellulose (HPMC), hydroxypropylcellulose (HPC) or hydroxyethylcellulose (HEC), preferably having an average viscosity (preferably measured by capillary viscosimetry or rotational viscosimetry) of 1,000 to 150,000 mPas, more preferably 3,000 to 150,000. In a preferred embodiment, the average viscosity is within the range of 110,000±50,000 mPas, more preferably 110,000±40,000 mPas, still more preferably 110,000±30,000 mPas, most preferably 110,000±20,000 mPas, and in particular 100,000±10,000 mPas.

In a preferred embodiment the relative weight ratio of said polyalkylene oxide (C) and said further polymer is within the range of from 20:1 to 1:20, more preferably 10:1 to 1:10, still more preferably 7:1 to 1:5, yet more preferably 5:1 to 1:1, most preferably 4:1 to 1,5:1 and in particular 3:1 to 2:1. In a preferred embodiment, the relative weight ratio of said polyalkylene oxide (C) and said further polymer is within the range of from 10:1 to 5:1, more preferably 8:1 to 5:1, most preferably 7:1 to 5:1.

Preferably, the content of said further polymer amounts to 0.5 to 25 wt.-%, more preferably 1.0 to 20 wt.-%, still more preferably 2.0 to 22.5 wt.-%, yet more preferably 3.0 to 20 wt.-% and most preferably 4.0 to 17.5 wt.-% and in particular 5.0 to 15 wt.-%, based on the total weight of the pharmaceutical dosage form.

In a preferred embodiment, the further polymer is a cellulose ester or cellulose ether, preferably HPMC, having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form.

In another preferred embodiment, the further polymer is a cellulose ester or cellulose ether, preferably HPMC, having a content within the range of 14±8 wt.-%, more preferably 14±6 wt.-%, still more preferably 14±5 wt.-%, yet more preferably 14±4 wt.-%, most preferably 14±3 wt.-%, and in particular 14±2 wt.-%, based on the total weight of the pharmaceutical dosage form.

All polymers are preferably employed as powders. They can be soluble in water.

Besides the pharmacologically active ingredient (A), the acid (B) and polyalkylene oxide (C) the pharmaceutical dosage form according to the invention may contain further constituents, such as conventional pharmaceutical excipients.

In a preferred embodiment, the pharmaceutical dosage form comprises an antioxidant. Suitable antioxidants include ascorbic acid, α-tocopherol (vitamin E), butylhydroxyanisol, butylhydroxytoluene, salts of ascorbic acid (vitamin C), ascorbylic palmitate, monothioglycerine, coniferyl benzoate, nordihydroguajaretic acid, gallus acid esters, phosphoric acid, and the derivatives thereof, such as vitamin E-succinate or vitamin E-palmitate and/or sodium bisulphite, more preferably butylhydroxytoluene (BHT) or butylhydroxyanisol (BHA) and/or α-tocopherol.

Preferably, the content of the antioxidant is within the range of from 0.001 to 5.0 wt.-%, more preferably 0.002 to 2.5 wt.-%, more preferably 0.003 to 1.5 wt.-%, still more preferably 0.005 to 1.0 wt.-%, yet more preferably 0.01 to 0.5 wt.-%, most preferably 0.05 to 0.4 wt.-% and in particular 0.1 to 0.3 wt.-%, based on the total weight of the pharmaceutical dosage form.

In a preferred embodiment, the content of the antioxidant is at most 5.0 wt.-%, more preferably at most 4.0 wt.-%, still more preferably at most 3.0 wt.-%, yet more preferably at most 2.0 wt.-%, even more preferably at most 1.0 wt.-%, most preferably at most 0.5 wt.-% and in particular at most 0.25 wt.-%, based on the total weight of the pharmaceutical dosage form.

A particularly preferred antioxidant is α-tocopherol. It has been surprisingly found that α-tocopherol stabilizes polyalkylene oxide and simultaneously destabilizes certain opioids (A), such as oxymorphone. Thus, in a preferred embodiment, the content of α-tocopherol is balanced between a sufficient stability of the polyalkylene oxide on the one hand and a sufficient stability of the pharmacologically active ingredient (A), preferably the opioid, on the other hand.

In a preferred embodiment, the content of α-tocopherol is within the range of 0.2±0.18 wt.-%, more preferably 0.2±0.15 wt.-%, still more preferably 0.2±0.12 wt.-%, yet more preferably 0.2±0.09 wt.-%, most preferably 0.2±0.06 wt.-%, and in particular 0.2±0.03 wt.-%, based on the total weight of the pharmaceutical dosage form.

In a preferred embodiment, the relative weight ratio of the acid (B), preferably citric acid, and the antioxidant, preferably α-tocopherol, is within the range of from 10:1 to 1:10, more preferably 8:1 to 1:8, still more preferably 6:1 to 1:6, yet more preferably 5:1 to 1:4, most preferably 4:1 to 1:3 and in particular 3:1 to 1:2.

In another preferred embodiment, the pharmaceutical dosage form does not comprise any of the antioxidants as defined above. Preferably, the pharmaceutical dosage form does neither contain butylhydroxytoluene (BHT), nor butylhydroxyanisol (BHA), nor α-tocopherol.

The pharmaceutical dosage form according to the invention may also contain a natural, semi-synthetic or synthetic wax. Waxes with a softening point of at least 50° C., more preferably 60° C. are preferred. Carnauba wax and beeswax are particularly preferred, especially carnauba wax.

Preferably, the release profile of the pharmacologically active ingredient (A), preferably the opioid, is matrix-retarded. Preferably, the pharmacologically active ingredient (A), preferably the opioid, is embedded in a matrix comprising the polyalkylene oxide, said matrix controlling the release of the pharmacologically active ingredient (A), preferably the opioid, from the pharmaceutical dosage form.

Physiologically acceptable materials which are known to the person skilled in the art may be used as supplementary matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, hydroxyethylcellulose, poly(meth)acrylic acid and/or the derivatives thereof, such as the salts, amides or esters thereof are very particularly preferably used as matrix materials. Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of $C_{12}$-$C_{30}$ fatty acids and/or $C_{12}$-$C_{30}$ fatty alcohols and/or waxes or mixtures thereof are particularly preferably used as hydrophobic materials. It is also possible to use mixtures of the above-stated hydrophilic and hydrophobic materials as matrix materials.

Preferably, the relative weight ratio of the polyalkylene oxide to the pharmacologically active ingredient (A), preferably the opioid, is at least 0.5:1, more preferably at least 1:1, at least 2:1, at least 3:1, at least 4:1, at least 5:1, at least 6:1, at least 7:1, at least 8:1 or at least 9:1; still more preferably at least 10:1 or at least 15:1, yet more preferably at least 20:1, most preferably at least 30:1 and in particular at least 40:1. In a preferred embodiment, the relative weight ratio of the polyalkylene oxide to the pharmacologically active ingredient (A), preferably the opioid, is within the range of from 3:1 to 50:1, more preferably 3:1 to 40:1 and in particular 3:1 to 30:1.

The pharmaceutical dosage form according to the invention preferably contains a plasticizer. The plasticizer improves the processability of the polyalkylene oxide. A preferred plasticizer is polyalkylene glycol, like polyethylene glycol, triacetin, fatty acids, fatty acid esters, waxes and/or microcrystalline waxes. Particularly preferred plasticizers are polyethylene glycols, such as PEG 6000.

Preferably, the content of the plasticizer is within the range of from 0.1 to 25 wt.-%, more preferably 0.5 to 22.5 wt.-%, still more preferably 1.0 to 20 wt.-%, yet more preferably 2.5 to 17.5 wt.-%, most preferably 5.0 to 15 wt.-% and in particular 7.5 to 12.5 wt.-%, based on the total weight of the pharmaceutical dosage form.

In a preferred embodiment, the plasticizer is a polyalkylene glycol having a content within the range of 10±8 wt.-%, more preferably 10±6 wt.-%, still more preferably 10±5 wt.-%, yet more preferably 10±4 wt.-%, most preferably 10±3 wt.-%, and in particular 10±2 wt.-%, based on the total weight of the pharmaceutical dosage form.

In another preferred embodiment, the plasticizer is a polyalkylene glycol having a content within the range of 15±8 wt.-%, more preferably 15±6 wt.-%, still more preferably 15±5 wt.-%, yet more preferably 15±4 wt.-%, most preferably 15±3 wt.-%, and in particular 15±2 wt.-%, based on the total weight of the pharmaceutical dosage form.

In a preferred embodiment, the relative weight ratio of the polyalkylene oxide to the polyalkylene glycol is within the range of 4.2±2:1, more preferably 4.2±1.5:1, still more preferably 4.2±1:1, yet more preferably 4.2±0.5:1, most preferably 4.2±0.2:1, and in particular 4.2±0.1:1. This ratio satisfies the requirements of relative high polyalkylene oxide content and good extrudability.

When manufacturing the dosage forms from slices that are obtained by cutting the extrudate strand, the weight of the slices determines the weight of the resulting dosage form. Pronounced variation in weight of these slices results in an accordant weight deviation of dosage forms from the target weight. The weight variation of slices depends strongly on the surface properties of the extrudate strand. A strand with a thoroughly smooth surface allows the generation of slices exhibiting a low weight variation. In contrast, a wavy or shark skinning strand results in slices exhibiting a higher weight variation thereby increasing the number of rejects.

It has now been surprisingly found that the surface properties of the extrudate strand can be triggered by the polyalkylene oxide:polyalkylene glycol weight ratio.

Preferred compositions $X_1$ to $X_{32}$ of the pharmaceutical dosage form according to the invention are summarized in the tables here below:

|  | wt.-% | | | |
| --- | --- | --- | --- | --- |
|  | $X_1$ | $X_2$ | $X_3$ | $X_4$ |
| pharmacologically active ingredient (A) (e.g. oxymorphone HCl) | 1.50 ± 1.25 | 1.50 ± 1.00 | 1.50 ± 0.75 | 1.50 ± 0.50 |
| acid (B) (e.g. citric acid) | 0.5 ± 0.30 | 0.5 ± 0.25 | 0.5 ± 0.20 | 0.5 ± 0.15 |
| polyalkylene oxide (C) | 77 ± 22 | 77 ± 20 | 77 ± 15 | 77 ± 10 |
| cellulose ester or ether (e.g. HPMC) | 12 ± 10 | 12 ± 7.5 | 12 ± 5 | 12 ± 2.5 |
| plasticizer (e.g. PEG) | 10 ± 7.5 | 10 ± 5 | 10 ± 2.5 | 10 ± 1.0 |
| antioxidant (e.g. α-tocopherol) | 0.2 ± 0.12 | 0.2 ± 0.1 | 0.2 ± 0.05 | 0.2 ± 0.03 |

-continued

|  | wt.-% | | | |
|---|---|---|---|---|
|  | $X_5$ | $X_6$ | $X_7$ | $X_8$ |
| pharmacologically active ingredient (A) (e.g. oxymorphone HCl) | 2.33 ± 1.25 | 2.33 ± 1.00 | 2.33 ± 0.75 | 2.33 ± 0.50 |
| acid (B) (e.g. citric acid) | 0.85 ± 0.60 | 0.85 ± 0.50 | 0.85 ± 0.25 | 0.85 ± 0.15 |
| polyalkylene oxide (C) | 70 ± 25 | 70 ± 20 | 70 ± 15 | 70 ± 10 |
| cellulose ester or ether (e.g. HPMC) | 10 ± 9.5 | 10 ± 7.5 | 10 ± 5 | 10 ± 2.5 |
| plasticizer (e.g. PEG) | 16.6 ± 7.5 | 16.6 ± 5 | 16.6 ± 2.5 | 16.6 ± 1.0 |
| antioxidant (e.g. α-tocopherol) | 0.2 ± 0.12 | 0.2 ± 0.1 | 0.2 ± 0.05 | 0.2 ± 0.03 |

|  | wt.-% | | | |
|---|---|---|---|---|
|  | $X_9$ | $X_{10}$ | $X_{11}$ | $X_{12}$ |
| pharmacologically active ingredient (A) (e.g. oxymorphone HCl) | 3.50 ± 1.25 | 3.50 ± 1.00 | 3.50 ± 0.75 | 3.50 ± 0.50 |
| acid (B) (e.g. citric acid) | 0.85 ± 0.60 | 0.85 ± 0.50 | 0.85 ± 0.25 | 0.85 ± 0.15 |
| polyalkylene oxide (C) | 69 ± 30 | 69 ± 20 | 69 ± 15 | 69 ± 10 |
| cellulose ester or ether (e.g. HPMC) | 10 ± 9.5 | 10 ± 7.5 | 10 ± 5 | 10 ± 2.5 |
| plasticizer (e.g. PEG) | 16.4 ± 7.5 | 16.4 ± 5 | 16.4 ± 2.5 | 16.4 ± 1.0 |
| antioxidant (e.g. α-tocopherol) | 0.2 ± 0.12 | 0.2 ± 0.1 | 0.2 ± 0.05 | 0.2 ± 0.03 |

|  | wt.-% | | | |
|---|---|---|---|---|
|  | $X_{13}$ | $X_{14}$ | $X_{15}$ | $X_{16}$ |
| pharmacologically active ingredient (A) (e.g. oxymorphone HCl) | 4.65 ± 1.25 | 4.65 ± 1.00 | 4.65 ± 0.75 | 4.65 ± 0.50 |
| acid (B) (e.g. citric acid) | 0.85 ± 0.60 | 0.85 ± 0.50 | 0.85 ± 0.25 | 0.85 ± 0.15 |
| polyalkylene oxide (C) | 68 ± 30 | 68 ± 20 | 68 ± 15 | 68 ± 10 |
| cellulose ester or ether (e.g. HPMC) | 10 ± 9.5 | 10 ± 7.5 | 10 ± 5 | 10 ± 2.5 |
| plasticizer (e.g. PEG) | 16.2 ± 7.5 | 16.2 ± 5 | 16.2 ± 2.5 | 16.2 ± 1.0 |
| antioxidant (e.g. α-tocopherol) | 0.2 ± 0.12 | 0.2 ± 0.1 | 0.2 ± 0.05 | 0.2 ± 0.03 |

|  | wt.-% | | | |
|---|---|---|---|---|
|  | $X_{17}$ | $X_{18}$ | $X_{19}$ | $X_{20}$ |
| pharmacologically active ingredient (A) (e.g. oxymorphone HCl) | 6.98 ± 1.25 | 6.98 ± 1.00 | 6.98 ± 0.75 | 6.98 ± 0.50 |
| acid (B) (e.g. citric acid) | 0.85 ± 0.60 | 0.85 ± 0.50 | 0.85 ± 0.25 | 0.85 ± 0.15 |
| polyalkylene oxide (C) | 66 ± 30 | 66 ± 20 | 66 ± 15 | 66 ± 10 |
| cellulose ester or ether (e.g. HPMC) | 10 ± 9.5 | 10 ± 7.5 | 10 ± 5 | 10 ± 2.5 |
| plasticizer (e.g. PEG) | 15.8 ± 7.5 | 15.8 ± 5 | 15.8 ± 2.5 | 15.8 ± 1.0 |
| antioxidant (e.g. α-tocopherol) | 0.2 ± 0.12 | 0.2 ± 0.1 | 0.2 ± 0.05 | 0.2 ± 0.03 |

|  | wt.-% | | | |
|---|---|---|---|---|
|  | $X_{21}$ | $X_{22}$ | $X_{23}$ | $X_{24}$ |
| pharmacologically active ingredient (A) (e.g. oxymorphone HCl) | 9.30 ± 1.25 | 9.30 ± 1.00 | 9.30 ± 0.75 | 9.30 ± 0.50 |
| acid (B) (e.g. citric acid) | 0.85 ± 0.60 | 0.85 ± 0.50 | 0.85 ± 0.25 | 0.85 ± 0.15 |
| polyalkylene oxide (C) | 64 ± 30 | 64 ± 20 | 64 ± 15 | 64 ± 10 |
| cellulose ester or ether (e.g. HPMC) | 10 ± 9.5 | 10 ± 7.5 | 10 ± 5 | 10 ± 2.5 |
| plasticizer (e.g. PEG) | 15.3 ± 7.5 | 15.3 ± 5 | 15.3 ± 2.5 | 15.3 ± 1.0 |
| antioxidant (e.g. α-tocopherol) | 0.2 ± 0.12 | 0.2 ± 0.1 | 0.2 ± 0.05 | 0.2 ± 0.03 |

|  | wt.-% | | | |
|---|---|---|---|---|
|  | $X_{25}$ | $X_{26}$ | $X_{27}$ | $X_{28}$ |
| pharmacologically active ingredient (A) (e.g. oxymorphone HCl) | 13.95 ± 1.25 | 13.95 ± 1.00 | 13.95 ± 0.75 | 13.95 ± 0.50 |
| acid (B) (e.g. citric acid) | 0.85 ± 0.60 | 0.85 ± 0.50 | 0.85 ± 0.25 | 0.85 ± 0.15 |
| polyalkylene oxide (C) | 60 ± 30 | 60 ± 20 | 60 ± 15 | 60 ± 10 |
| cellulose ester or ether (e.g. HPMC) | 10 ± 9.5 | 10 ± 7.5 | 10 ± 5 | 10 ± 2.5 |
| plasticizer (e.g. PEG) | 13.9 ± 7.5 | 13.9 ± 5 | 13.9 ± 2.5 | 13.9 ± 1.0 |
| antioxidant (e.g. α-tocopherol) | 0.2 ± 0.12 | 0.2 ± 0.1 | 0.2 ± 0.05 | 0.2 ± 0.03 |

|  | wt.-% | | | |
|---|---|---|---|---|
|  | $X_{29}$ | $X_{30}$ | $X_{31}$ | $X_{32}$ |
| pharmacologically active ingredient (A) (e.g. oxymorphone HCl) | 18.60 ± 1.25 | 18.60 ± 1.00 | 18.60 ± 0.75 | 18.60 ± 0.50 |

| -continued | | | | |
|---|---|---|---|---|
| acid (B) (e.g. citric acid) | 0.85 ± 0.60 | 0.85 ± 0.50 | 0.85 ± 0.25 | 0.85 ± 0.15 |
| polyalkylene oxide (C) | 57 ± 30 | 57 ± 20 | 57 ± 15 | 57 ± 10 |
| cellulose ester or ether (e.g. HPMC) | 10 ± 9.5 | 10 ± 7.5 | 10 ± 5 | 10 ± 2.5 |
| plasticizer (e.g. PEG) | 13.6 ± 7.5 | 13.6 ± 5 | 13.6 ± 2.5 | 13.6 ± 1.0 |
| antioxidant (e.g. α-tocopherol) | 0.2 ± 0.12 | 0.2 ± 0.1 | 0.2 ± 0.05 | 0.2 ± 0.03 |

In a preferred embodiment, the pharmaceutical dosage form has a total weight within the range of 100±75 mg, more preferably 100±50 mg, most preferably 100±25 mg. In another preferred embodiment, the pharmaceutical dosage form has a total weight within the range of 200±75 mg, more preferably 200±50 mg, most preferably 200±25 mg. In another preferred embodiment, the pharmaceutical dosage form has a total weight within the range of 250±75 mg, more preferably 250±50 mg, most preferably 250±25 mg. In still another preferred embodiment, the pharmaceutical dosage form has a total weight within the range of 300±75 mg, more preferably 300±50 mg, most preferably 300±25 mg. In yet another preferred embodiment, the pharmaceutical dosage form has a total weight within the range of 400±75 mg, more preferably 400±50 mg, most preferably 400±25 mg.

In a preferred embodiment, the pharmaceutical dosage form has a total weight within the range of 500±250 mg, more preferably 500±200 mg, most preferably 500±150 mg. In another preferred embodiment, the pharmaceutical dosage form has a total weight within the range of 750±250 mg, more preferably 750±200 mg, most preferably 750±150 mg. In another preferred embodiment, the pharmaceutical dosage form has a total weight within the range of 1000±250 mg, more preferably 1000±200 mg, most preferably 1000±150 mg. In still another preferred embodiment, the pharmaceutical dosage form has a total weight within the range of 1250±250 mg, more preferably 1250±200 mg, most preferably 1250±150 mg.

In a preferred embodiment, the pharmaceutical dosage form according to the invention has an overall density within the range of 1.19±0.30 g/cm$^3$, more preferably 1.19±0.25 g/cm$^3$, still more preferably 1.19±0.20 g/cm$^3$, yet more preferably 1.19±0.15 g/cm$^3$, most preferably 1.19±0.10 g/cm$^3$, and in particular 1.19±0.05 g/cm$^3$. Preferably, the overall density of the pharmaceutical dosage form according to the invention is within the range of 1.17±0.02 g/cm$^3$, 1.19±0.02 or 1.21±0.02. Methods for measuring the density of a dosage form are known to a person skilled in the art. The overall density of a dosage form can for example be determined by means of the mercury porosimetry method or the helium pycnometer method, as described in Ph. Eur.

Preferably, the pharmaceutical dosage form according to the invention is adapted for oral administration. It is also possible, however, to administer the pharmaceutical dosage form via different routes and thus, the pharmaceutical dosage form may alternatively be adapted for buccal, lingual, rectal or vaginal administration. Implants are also possible.

In a preferred embodiment, the pharmaceutical dosage form according to the invention is adapted for administration once daily. In another preferred embodiment, the pharmaceutical dosage form according to the invention is adapted for administration twice daily. In still another preferred embodiment, the pharmaceutical dosage form according to the invention is adapted for administration thrice daily.

For the purpose of the specification, "twice daily" means equal or nearly equal time intervals, i.e., about every 12 hours, or different time intervals, e.g., 8 and 16 hours or 10 and 14 hours, between the individual administrations.

For the purpose of the specification, "thrice daily" means equal or nearly equal time intervals, i.e., about every 8 hours, or different time intervals, e.g., 6, 6 and 12 hours; or 7, 7 and 10 hours, between the individual administrations.

Preferably, the pharmaceutical dosage form according to the invention causes an at least partially delayed or prolonged release of the pharmacologically active ingredient (A), preferably opioid (A).

Controlled or prolonged release is understood according to the invention preferably to mean a release profile in which the pharmacologically active ingredient (A), preferably the opioid, is released over a relatively long period with reduced intake frequency with the purpose of extended therapeutic action. Preferably, the meaning of the term "prolonged release" is in accordance with the European guideline on the nomenclature of the release profile of pharmaceutical dosage forms (CHMP). This is achieved in particular with peroral administration. The expression "at least partially delayed or prolonged release" covers according to the invention any pharmaceutical dosage forms which ensure modified release of the pharmacologically active ingredients (A), preferably the opioids, contained therein. The pharmaceutical dosage forms preferably comprise coated or uncoated pharmaceutical dosage forms, which are produced with specific auxiliary substances, by particular processes or by a combination of the two possible options in order purposefully to change the release rate or location of release.

In the case of the pharmaceutical dosage forms according to the invention, the release time profile of a controlled release form may be modified e.g. as follows: extended release, repeat action release, prolonged release and sustained release.

For the purpose of the specification "controlled release" preferably means a product in which the release of active compound over time is controlled by the type and composition of the formulation. For the purpose of the specification "extended release" preferably means a product in which the release of active compound is delayed for a finite lag time, after which release is unhindered. For the purpose of the specification "repeat action release" preferably means a product in which a first portion of active compound is released initially, followed by at least one further portion of active compound being released subsequently. For the purpose of the specification "prolonged release" preferably means a product in which the rate of release of active compound from the formulation after administration has been reduced over time, in order to maintain therapeutic activity, to reduce toxic effects, or for some other therapeutic purpose. For the purpose of the specification "sustained release" preferably means a way of formulating a medicine so that it is released into the body steadily, over a long period of time, thus reducing the dosing frequency. For further details, reference may be made, for example, to K. H. Bauer, Lehrbuch der Pharmazeutischen Technologie, 6th edition, WVG Stuttgart, 1999; and Eur. Ph.

The pharmaceutical dosage form according to the invention may comprise one or more pharmacologically active ingredients (A), preferably opioids, at least in part in a further controlled release form, wherein controlled release may be achieved with the assistance of conventional materials and processes known to the person skilled in the art, for example by embedding the substance in a controlled release matrix or by applying one or more controlled release coatings. Substance release must, however, be controlled such that addition of delayed-release materials does not impair the necessary breaking strength. Controlled release from the pharmaceutical dosage form according to the invention is preferably achieved by embedding the substance in a matrix. Preferably, polyalkylene oxide (C) serves as such a matrix. The auxiliary substances acting as matrix materials control release. Matrix materials may, for example, be hydrophilic, gel-forming materials, from which release proceeds mainly by diffusion, or hydrophobic materials, from which release proceeds mainly by diffusion from the pores in the matrix.

Preferably, the release profile is substantially matrix controlled, preferably by embedding pharmacologically active ingredient (A), preferably opioid (A), in a matrix comprising polyalkylene oxide (C) and optionally, further matrix materials. Preferably, the release profile is not osmotically driven. Preferably, release kinetics is not zero order.

Preferably, under physiological conditions the pharmaceutical dosage form according to the invention has released after 30 minutes 0.1 to 75%, after 240 minutes 0.5 to 95%, after 480 minutes 1.0 to 100% and after 720 minutes 2.5 to 100% of the pharmacologically active ingredient (A), preferably opioid (A). Further preferred release profiles $R_1$ to $R_6$ are summarized in the table here below [all data in wt.-% of released pharmacologically active ingredient (A), preferably opioid (A)]:

| time | $R_1$ | $R_2$ | $R_3$ | $R_4$ | $R_5$ | $R_6$ |
|---|---|---|---|---|---|---|
| 60 min | 0-30 | 0-50 | 0-50 | 15-25 | 20-30 | 20-50 |
| 120 min | 0-40 | 0-75 | 0-75 | 25-40 | 35-50 | 40-75 |
| 240 min | 3-55 | 3-95 | 10-95 | 40-70 | 55-75 | 60-95 |
| 480 min | 10-65 | 10-100 | 35-100 | 60-90 | 80-95 | 80-100 |
| 720 min | 20-75 | 20-100 | 55-100 | 70-100 | 90-100 | 90-100 |
| 960 min | 30-88 | 30-100 | 70-100 | >80 | 95-100 | |
| 1440 min | 50-100 | 50-100 | >90 | | | |
| 2160 min | >80 | >80 | | | | |

Further preferred release profiles $R_1$ to $R_6$ are summarized in the table here below [all data in wt.-% of released pharmacologically active ingredient (A), preferably opioid (A)]:

| time | $R_7$ | $R_8$ | $R_9$ | $R_{10}$ | $R_{11}$ | $R_{12}$ |
|---|---|---|---|---|---|---|
| 30 min | 17.5 ± 7.5 | 17.5 ± 6.5 | 17.5 ± 5.5 | 17.5 ± 4.5 | 17.5 ± 3.5 | 17.5 ± 2.5 |
| 60 min | 27.0 ± 8.0 | 27.0 ± 7.0 | 27.0 ± 6.0 | 27.0 ± 5.0 | 27.0 ± 4.0 | 27.0 ± 3.0 |
| 120 min | 41.5 ± 9.5 | 41.5 ± 8.5 | 41.5 ± 7.5 | 41.5 ± 6.5 | 41.5 ± 5.5 | 41.5 ± 4.5 |
| 240 min | 64.5 ± 12.5 | 64.5 ± 11.5 | 64.5 ± 10.5 | 64.5 ± 9.5 | 64.5 ± 8.5 | 64.5 ± 7.5 |
| 480 min | 88.0 ± 12.0 | 88.0 ± 11.0 | 88.0 ± 10.0 | 88.0 ± 9.0 | 88.0 ± 8.0 | 88.0 ± 7.0 |
| 720 min | 96.0 ± 9.0 | 96.0 ± 8.0 | 96.0 ± 7.0 | 96.0 ± 6.0 | 96.0 ± 5.0 | 96.0 ± 4.0 |
| 840 min | 97.5 ± 7.5 | 97.5 ± 6.5 | 97.5 ± 5.5 | 97.5 ± 4.5 | 97.5 ± 3.5 | 97.5 ± 2.5 |

Preferably, the release profile of the pharmaceutical dosage form according to the present invention is stable upon storage, preferably upon storage at elevated temperature, e.g. 37° C., for 3 months in sealed containers. In this regard "stable" means that when comparing the initial release profile with the release profile after storage, at any given time point the release profiles deviate from one another by not more than 20%, more preferably not more than 15%, still more preferably not more than 10%, yet more preferably not more than 7.5%, most preferably not more than 5.0% and in particular not more than 2.5%.

Preferably, under in vitro conditions the pharmaceutical dosage form has released after 0.5 h 1.0 to 35 wt.-%, after 1 h 5.0 to 45 wt.-%, after 2 h 10 to 60 wt.-%, after 4 h at least 15 wt.-%, after 6 h at least 20 wt.-%, after 8 h at least 25 wt.-% and after 12 h at least 30 wt.-% of the pharmacologically active ingredient (A), preferably the opioid, that was originally contained in the pharmaceutical dosage form.

Suitable in vitro conditions are known to the skilled artisan. In this regard it can be referred to, e.g., the Eur. Ph. Preferably, the release profile is measured under the following conditions: Paddle apparatus equipped with sinker, 50 rpm, 37±5° C., 900 mL simulated intestinal fluid pH 6.8 (phosphate buffer) or pH 4.5. In a preferred embodiment, to rotational speed of the paddle is increased to 100 rpm.

In a preferred embodiment, after preferably oral administration of the pharmaceutical dosage form according to the invention, in vivo the average peak plasma level ($C_{max}$) is on average reached after $t_{max}$ 4.0±2.5 h, more preferably after $t_{max}$ 4.0±2.0 h, still more preferably after $t_{max}$ 4.0±1.5 h, most preferably after $t_{max}$ 4.0±1.0 h and in particular after $t_{max}$ 4.0±0.5 h. In another preferred embodiment, after preferably oral administration of the pharmaceutical dosage form according to the invention, in vivo the average peak plasma level ($C_{max}$) is on average reached after $t_{max}$ 5.0±2.5 h, more preferably after $t_{max}$ 5.0±2.0 h, still more preferably after $t_{max}$ 5.0±1.5 h, most preferably after $t_{max}$ 5.0±1.0 h and in particular after $t_{max}$ 5.0±0.5 h. In still another preferred embodiment, after preferably oral administration of the pharmaceutical dosage form according to the invention, in vivo the average peak plasma level ($C_{max}$) is on average reached after $t_{max}$ 6.0±2.5 h, more preferably after $t_{max}$ 6.0±2.0 h, still more preferably after $t_{max}$ 6.0±1.5 h, most preferably after $t_{max}$ 6.0±1.0 h and in particular after $t_{max}$ 6.0±0.5 h.

In a preferred embodiment, the average value for $t_{1/2}$ after preferably oral administration of the pharmaceutical dosage form according to the invention in vivo is 4.0±2.5 h, more preferably 4.0±2.0 h, still more preferably 4.0±1.5 h, most preferably 4.0±1.0 h, and in particular 4.0±0.5 h. In another preferred embodiment, the average value for $t_{1/2}$ after preferably oral administration of the pharmaceutical dosage form according to the invention in vivo is preferably 5.0±2.5 h, more preferably 5.0±2.0 h, still more preferably 5.0±1.5 h, most preferably 5.0±1.0 h, and in particular 5.0±0.5 h. In still another preferred embodiment, the average value for $t_{1/2}$ after preferably oral administration of the pharmaceutical dosage form according to the invention in vivo is preferably 6.0±2.5 h, more preferably 6.0±2.0 h, still more preferably 6.0±1.5 h, most preferably 6.0±1.0 h, and in particular 6.0±0.5 h.

Preferably, the pharmaceutical dosage form according to the invention contains a coating, preferably a film-coating. Suitable coating materials are known to the skilled person.

Suitable coating materials are commercially available, e.g. under the trademarks Opadry® and Eudragit®.

Examples of suitable materials include cellulose esters and cellulose ethers, such as methylcellulose (MC), hydroxypropylmethylcellulose (HPMC), hydroxypropylcellulose (HPC), hydroxyethylcellulose (HEC), sodium carboxymethylcellulose (Na-CMC), ethylcellulose (EC), cellulose acetate phthalate (CAP), hydroxypropylmethylcellulose phthalate (HPMCP); poly(meth)acrylates, such as aminoalkylmethacrylate copolymers, ethylacrylate methylmethacrylate copolymers, methacrylic acid methylmethacrylate copolymers, methacrylic acid methylmethacrylate copolymers; vinyl polymers, such as polyvinylpyrrolidone, polyvinylacetatephthalate, polyvinyl alcohol, polyvinylacetate; and natural film formers, such as shellack.

In a particularly preferred embodiment, the coating is water-soluble. In a preferred embodiment, the coating is based on polyvinyl alcohol, such as polyvinyl alcohol-part. hydrolyzed, and may additionally contain polyethylene glycol, such as macrogol 3350, and/or pigments. In another preferred embodiment, the coating is based on hydroxypropylmethylcellulose, preferably hypromellose type 2910 having a viscosity of 3 to 15 mPas.

The coating of the pharmaceutical dosage form can increase its storage stability.

The coating can be resistant to gastric juices and dissolve as a function of the pH value of the release environment. By means of this coating, it is possible to ensure that the pharmaceutical dosage form according to the invention passes through the stomach undissolved and the active compound is only released in the intestines. The coating which is resistant to gastric juices preferably dissolves at a pH value of between 5 and 7.5. Corresponding materials and methods for the delayed release of active compounds and for the application of coatings which are resistant to gastric juices are known to the person skilled in the art, for example from "Coated Pharmaceutical dosage forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers.

In a preferred embodiment, the pharmaceutical dosage form according to the invention contains no substances which irritate the nasal passages and/or pharynx, i.e. substances which, when administered via the nasal passages and/or pharynx, bring about a physical reaction which is either so unpleasant for the patient that he/she does not wish to or cannot continue administration, for example burning, or physiologically counteracts taking of the corresponding active compound, for example due to increased nasal secretion or sneezing. Further examples of substances which irritate the nasal passages and/or pharynx are those which cause burning, itching, urge to sneeze, increased formation of secretions or a combination of at least two of these stimuli. Corresponding substances and the quantities thereof which are conventionally to be used are known to the person skilled in the art. Some of the substances which irritate the nasal passages and/or pharynx are accordingly based on one or more constituents or one or more plant parts of a hot substance drug. Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer Verlag, Stuttgart-New York, 1982, pages 82 et seq. The corresponding description is hereby introduced as a reference and is deemed to be part of the disclosure.

The pharmaceutical dosage form according to the invention furthermore preferably contains no antagonists for the pharmacologically active ingredient (A), preferably no opioid antagonists more preferably no antagonists against psychotropic substances, in particular no antagonists against opioids (A). Antagonists suitable for a given pharmacologically active ingredient (A) are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no antagonists selected from among the group comprising naloxone, naltrexone, nalmefene, nalide, nalmexone, nalorphine or naluphine, in each case optionally in the form of a corresponding physiologically acceptable compound, in particular in the form of a base, a salt or solvate; and no neuroleptics, for example a compound selected from among the group comprising haloperidol, promethacine, fluphenazine, perphenazine, levomepromazine, thioridazine, perazine, chlorpromazine, chlorprothixine, zuclopenthixol, flupentixol, prothipendyl, zotepine, benperidol, pipamperone, melperone and bromperidol.

The pharmaceutical dosage form according to the invention furthermore preferably contains no emetic. Emetics are known to the person skilled in the art and may be present as such or in the form of corresponding derivatives, in particular esters or ethers, or in each case in the form of corresponding physiologically acceptable compounds, in particular in the form of the salts or solvates thereof. The pharmaceutical dosage form according to the invention preferably contains no emetic based on one or more constituents of ipecacuanha (ipecac) root, for example based on the constituent emetine, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, N.Y., 1982. The corresponding literature description is hereby introduced as a reference and is deemed to be part of the disclosure. The pharmaceutical dosage form according to the invention preferably also contains no apomorphine as an emetic.

Finally, the pharmaceutical dosage form according to the invention preferably also contains no bitter substance. Bitter substances and the quantities effective for use may be found in US-2003/0064099 A1, the corresponding disclosure of which should be deemed to be the disclosure of the present application and is hereby introduced as a reference. Examples of bitter substances are aromatic oils, such as peppermint oil, eucalyptus oil, bitter almond oil, menthol, fruit aroma substances, aroma substances from lemons, oranges, limes, grapefruit or mixtures thereof, and/or denatonium benzoate.

The pharmaceutical dosage form according to the invention accordingly preferably contains neither substances which irritate the nasal passages and/or pharynx, nor antagonists for the pharmacologically active ingredient (A), preferably the opioid (A), nor emetics, nor bitter substances.

The pharmaceutical dosage form according to the invention is preferably adapted for oral administration.

Typically, the pharmaceutical dosage form according to the invention assumes the form of a tablet. Preferably, the pharmaceutical dosage form is neither in film form, nor multi-particulate.

The pharmaceutical dosage form according to the invention is preferably tamper-resistant. Preferably, tamper-resistance is achieved based on the mechanical properties of the pharmaceutical dosage form so that comminution is avoided or at least substantially impeded. According to the invention, the term comminution means the pulverization of the pharmaceutical dosage form using conventional means usually available to an abuser, for example a pestle and mortar, a hammer, a mallet or other conventional means for pulverizing under the action of force. Thus, tamper-resistance preferably means that pulverization of the pharmaceutical dosage form using conventional means is avoided or at least substantially impeded.

Preferably, the mechanical properties of the pharmaceutical dosage form according to the invention, particularly its breaking strength, substantially rely on the presence and spatial distribution of polyalkylene oxide (C), although its mere presence does typically not suffice in order to achieve said properties. The advantageous mechanical properties of the pharmaceutical dosage form according to the invention may not automatically be achieved by simply processing pharmacologically active ingredient (A), acid (B), polyalkylene oxide (C), and optionally further excipients by means of conventional methods for the preparation of pharmaceutical dosage forms. In fact, usually suitable apparatuses must be selected for the preparation and critical processing parameters must be adjusted, particularly pressure/force, temperature and time. Thus, even if conventional apparatuses are used, the process protocols usually must be adapted in order to meet the required criteria.

The pharmaceutical dosage form according to the invention has a breaking strength of at least 300 N, preferably at least 400 N, more preferably at least 500 N, still more preferably at least 750 N, yet more preferably at least 1000 N, most preferably at least 1250 N and in particular at least 1500 N.

The "breaking strength" (resistance to crushing) of a pharmaceutical dosage form is known to the skilled person. In this regard it can be referred to, e.g., W. A. Ritschel, Die Tablette, 2. Auflage, Edition Cantor Verlag Aulendorf, 2002; H Liebermann et al., Pharmaceutical dosage forms: Tablets, Vol. 2, Informa Healthcare; 2 edition, 1990; and Encyclopedia of Pharmaceutical Technology, Informa Healthcare; 1 edition.

For the purpose of the specification, the breaking strength is preferably defined as the amount of force that is necessary in order to fracture the pharmaceutical dosage form (=breaking force). Therefore, for the purpose of the specification the pharmaceutical dosage form does preferably not exhibit the desired breaking strength when it breaks, i.e., is fractured into at least two independent parts that are separated from one another. In another preferred embodiment, however, the pharmaceutical dosage form is regarded as being broken if the force decreases by 25% (threshold value) of the highest force measured during the measurement (see below).

The pharmaceutical dosage forms according to the invention are distinguished from conventional pharmaceutical dosage forms in that, due to their breaking strength, they cannot be pulverized by the application of force with conventional means, such as for example a pestle and mortar, a hammer, a mallet or other usual means for pulverization, in particular devices developed for this purpose (tablet crushers). In this regard "pulverization" means crumbling into small particles that would immediately release the pharmacologically active compound (A), preferably the opioid, in a suitable medium.

Avoidance of pulverization virtually rules out oral or parenteral, in particular intravenous or nasal abuse.

Conventional tablets typically have a breaking strength well below 200 N in any direction of extension. The breaking strength of conventional round tablets may be estimated according to the following empirical formula: Breaking Strength [in N]=10×Diameter Of The Tablet [in mm]. Thus, according to said empirical formula, a round tablet having a breaking strength of at least 300 N would require a diameter of at least 30 mm). Such a tablet, however, could not be swallowed. The above empirical formula preferably does not apply to the pharmaceutical dosage forms of the invention, which are not conventional but rather special.

Further, the actual mean chewing force is about 220 N (cf., e.g., P. A. Proeschel et al., J Dent Res, 2002, 81(7), 464-468). This means that conventional tablets having a breaking strength well below 200 N may be crushed upon spontaneous chewing, whereas the pharmaceutical dosage forms according to the invention may not.

Still further, when applying a gravitational acceleration of about 9.81 m/s$^2$, 300 N correspond to a gravitational force of more than 30 kg, i.e. the pharmaceutical dosage forms according to the invention can preferably withstand a weight of more than 30 kg without being pulverised.

Methods for measuring the breaking strength of a pharmaceutical dosage form are known to the skilled artisan. Suitable devices are commercially available.

For example, the breaking strength (resistance to crushing) can be measured in accordance with the Eur. Ph. 5.0, 2.9.8 or 6.0, 2.09.08 "Resistance to Crushing of Tablets". The test is intended to determine, under defined conditions, the resistance to crushing of tablets, measured by the force needed to disrupt them by crushing. The apparatus consists of 2 jaws facing each other, one of which moves towards the other. The flat surfaces of the jaws are perpendicular to the direction of movement. The crushing surfaces of the jaws are flat and larger than the zone of contact with the tablet. The apparatus is calibrated using a system with a precision of 1 Newton. The tablet is placed between the jaws, taking into account, where applicable, the shape, the break-mark and the inscription; for each measurement the tablet is oriented in the same way with respect to the direction of application of the force (and the direction of extension in which the breaking strength is to be measured). The measurement is carried out on 10 tablets, taking care that all fragments of tablets have been removed before each determination. The result is expressed as the mean, minimum and maximum values of the forces measured, all expressed in Newton.

A similar description of the breaking strength (breaking force) can be found in the USP. The breaking strength can alternatively be measured in accordance with the method described therein where it is stated that the breaking strength is the force required to cause a tablet to fail (i.e., break) in a specific plane. The tablets are generally placed between two platens, one of which moves to apply sufficient force to the tablet to cause fracture. For conventional, round (circular cross-section) tablets, loading occurs across their diameter (sometimes referred to as diametral loading), and fracture occurs in the plane. The breaking force of tablets is commonly called hardness in the pharmaceutical literature; however, the use of this term is misleading. In material science, the term hardness refers to the resistance of a surface to penetration or indentation by a small probe. The term crushing strength is also frequently used to describe the resistance of tablets to the application of a compressive load. Although this term describes the true nature of the test more accurately than does hardness, it implies that tablets are actually crushed during the test, which is often not the case.

Alternatively, the breaking strength (resistance to crushing) can be measured in accordance with WO 2005/016313, WO 2005/016314, and WO 2006/082099, which can be regarded as a modification of the method described in the Eur. Ph. The apparatus used for the measurement is preferably a "Zwick Z 2.5" materials tester, $F_{max}$=2.5 kN with a maximum draw of 1150 mm, which should be set up with one column and one spindle, a clearance behind of 100 mm and a test speed adjustable between 0.1 and 800 mm/min together with testControl software. Measurement is performed using a pressure piston with screw-in inserts and a cylinder (diameter 10 mm), a force transducer, $F_{max}$. 1 kN, diameter=8 mm, class 0.5 from 10 N, class 1 from 2 N to ISO 7500-1, with manufacturers test certificate M according to DIN 55350-18 (Zwick gross force $F_{max}$=1.45 kN) (all apparatus from Zwick GmbH & Co. KG, Ulm, Germany) with Order No BTC-FR 2.5 TH. D09 for the tester, Order No BTC-LC 0050N. P01 for the force transducer, Order No BO 70000 S06 for the centring device.

In a preferred embodiment of the invention, the breaking strength is measured by means of a breaking strength tester e.g. Sotax®, type HT100 or type HT1 (Allschwil, Switzerland). Both, the Sotax® HT100 and the Sotax® HT1 can measure the breaking strength according to two different measurement principles: constant speed (where the test jaw is moved at a constant speed adjustable from 5-200 mm/min) or constant force (where the test jaw increases force linearly adjustable from 5-100 N/sec). In principle, both measurement principles are suitable for measuring the breaking strength of the pharmaceutical dosage form according to the invention. Preferably, the breaking strength is measured at constant speed, preferably at a constant speed of 120 mm/min.

In a preferred embodiment, the pharmaceutical dosage form is regarded as being broken if it is fractured into at least two separate pieces.

The pharmaceutical dosage form according to the invention preferably exhibits mechanical strength over a wide temperature range, in addition to the breaking strength (resistance to crushing) optionally also sufficient hardness, impact resistance, impact elasticity, tensile strength and/or modulus of elasticity, optionally also at low temperatures (e.g. below −24° C., below −40° C. or in liquid nitrogen), for it to be virtually impossible to pulverize by spontaneous chewing, grinding in a mortar, pounding, etc. Thus, preferably, the comparatively high breaking strength of the pharmaceutical dosage form according to the invention is maintained even at low or very low temperatures, e.g., when the pharmaceutical dosage form is initially chilled to increase its brittleness, for example to temperatures below −25° C., below −40° C. or even in liquid nitrogen.

The pharmaceutical dosage form according to the invention is characterized by a certain degree of breaking strength. This does not mean that the pharmaceutical dosage form must also exhibit a certain degree of hardness. Hardness and breaking strength are different physical properties. Therefore, the tamper resistance of the pharmaceutical dosage form does not necessarily depend on the hardness of the pharmaceutical dosage form. For instance, due to its breaking strength, impact strength, elasticity modulus and tensile strength, respectively, the pharmaceutical dosage form can preferably be deformed, e.g. plastically, when exerting an external force, for example using a hammer, but cannot be pulverized, i.e., crumbled into a high number of fragments. In other words, the pharmaceutical dosage form according to the invention is characterized by a certain degree of breaking strength, but not necessarily also by a certain degree of form stability.

Therefore, in the meaning of the specification, a pharmaceutical dosage form that is deformed when being exposed to a force in a particular direction of extension but that does not break (plastic deformation or plastic flow) is preferably to be regarded as having the desired breaking strength in said direction of extension.

A particularly preferred embodiment of the invention relates to a tamper-resistant pharmaceutical dosage form having a breaking strength of at least 300 N and being thermoformed by hot-melt extrusion, said pharmaceutical dosage form comprising a pharmacologically active ingredient (A), preferably an opioid, particularly preferred an opioid selected from the group consisting of oxymorphone, oxycodone, hydromorphone, and the physiologically acceptable salts thereof;

a free physiologically acceptable multicarboxylic acid (B), preferably citric acid, wherein the content of the acid (B) is within the range of from 0.001 to 5.0 wt.-%, based on the total weight of the pharmaceutical dosage form;

an antioxidant, wherein the content of the antioxidant, preferably α-tocopherol, is within the range of from 0.001 to 5.0 wt.-%, based on the total weight of the pharmaceutical dosage form; and a polyalkylene oxide (C) having a weight average molecular weight $M_w$ of at least 200,000 g/mol;

wherein the pharmacologically active ingredient (A) is embedded in a matrix comprising the polyalkylene oxide (C), said matrix controlling the release of the pharmacologically active ingredient (A) from the pharmaceutical dosage form; and after storage for 4 weeks at 40° C. and 75% rel. humidity, the content of pharmacologically active ingredient (A), preferably opioid (A), amounts to at least 98.0% of its original content before storage.

The pharmaceutical dosage form according to the invention may be produced by different processes, the particularly preferred of which are explained in greater detail below. Several suitable processes have already been described in the prior art. In this regard it can be referred to, e.g., WO 2005/016313, WO 2005/016314, WO 2005/063214, WO 2005/102286, WO 2006/002883, WO 2006/002884, WO 2006/002886, WO 2006/082097, and WO 2006/082099.

The present invention also relates to pharmaceutical dosage forms that are obtainable by any of the processes described here below.

In general, the process for the production of the pharmaceutical dosage form according to the invention preferably comprises the following steps:

(a) mixing all ingredients;
(b) optionally pre-forming the mixture obtained from step (a), preferably by applying heat and/or force to the mixture obtained from step (a), the quantity of heat supplied preferably not being sufficient to heat the polyalkylene oxide (C) up to its softening point;
(c) hardening the mixture by applying heat and force, it being possible to supply the heat during and/or before the application of force and the quantity of heat supplied being sufficient to heat the polyalkylene oxide (C) at least up to its softening point;
(d) optionally singulating the hardened mixture;
(e) optionally shaping the pharmaceutical dosage form; and
(f) optionally providing a film coating.

Heat may be supplied directly, e.g. by contact or by means of hot gas such as hot air, or with the assistance of ultrasound. Force may be applied and/or the pharmaceutical dosage form may be shaped for example by direct tabletting or with the assistance of a suitable extruder, particularly by means of a screw extruder equipped with two screws (twin-screw-extruder) or by means of a planetary gear extruder.

The final shape of the pharmaceutical dosage form may either be provided during the hardening of the mixture by applying heat and force (step (c)) or in a subsequent step (step (e)). In both cases, the mixture of all components is preferably in the plastified state, i.e. preferably, shaping is performed at a temperature at least above the softening point of the polyalkylene oxide (C). However, extrusion at lower temperatures, e.g. ambient temperature, is also possible and may be preferred.

Shaping can be performed, e.g., by means of a tabletting press comprising die and punches of appropriate shape.

A particularly preferred process for the manufacture of the pharmaceutical dosage form of the invention involves hotmelt extrusion. In this process, the pharmaceutical dosage form according to the invention is produced by thermoforming with the assistance of an extruder, preferably without there being any observable consequent discoloration of the extrudate. It has been surprisingly found that acid (B) is capable of suppressing discoloration. In the absence of acid (B), the extrudate tends to develop beige to yellowish coloring whereas in the presence of acid (B) the extrudates are substantially colorless, i.e. white.

This process is characterized in that
a) all components are mixed,
b) the resultant mixture is heated in the extruder at least up to the softening point of the polyalkylene oxide (C) and extruded through the outlet orifice of the extruder by application of force,
c) the still plastic extrudate is singulated and formed into the pharmaceutical dosage form or
d) the cooled and optionally reheated singulated extrudate is formed into the pharmaceutical dosage form.

Mixing of the components according to process step a) may also proceed in the extruder.

The components may also be mixed in a mixer known to the person skilled in the art. The mixer may, for example, be a roll mixer, shaking mixer, shear mixer or compulsory mixer.

Before blending with the remaining components, polyalkylene oxide (C) is preferably provided according to the invention with an antioxidant, preferably α-tocopherol. This may proceed by mixing the two components, the polyalkylene oxide (C) and the antioxidant, preferably by dissolving or suspending the antioxidant in a highly volatile solvent and homogeneously mixing this solution or suspension with polyalkylene oxide (C) and removing the solvent by drying, preferably under an inert gas atmosphere.

The preferably molten, mixture which has been heated in the extruder at least up to the softening point of polyalkylene oxide (C) is extruded from the extruder through a die with at least one bore.

The process according to the invention requires the use of suitable extruders, preferably screw extruders. Screw extruders which are equipped with two screws (twin-screw-extruders) are particularly preferred.

The extrusion is preferably performed so that the expansion of the strand due to extrusion is not more than 30%, i.e. that when using a die with a bore having a diameter of e.g. 6 mm, the extruded strand should have a diameter of not more than 8 mm. More preferably, the expansion of the strand is not more than 25%, still more preferably not more than 20%, most preferably not more than 15% and in particular not more than 10%.

Preferably, extrusion is performed in the absence of water, i.e., no water is added. However, traces of water (e.g., caused by atmospheric humidity) may be present.

The extruder preferably comprises at least two temperature zones, with heating of the mixture at least up to the softening point of the polyalkylene oxide (C) proceeding in the first zone, which is downstream from a feed zone and optionally mixing zone. The throughput of the mixture is preferably from 1.0 kg to 15 kg/hour. In a preferred embodiment, the throughput is from 1 to 3.5 kg/hour. In another preferred embodiment, the throughput is from 4 to 15 kg/hour.

In a preferred embodiment, the die head pressure is within the range of from 25 to 100 bar. The die head pressure can be adjusted inter alia by die geometry, temperature profile and extrusion speed.

The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of the polyalkylene oxide (C) and does not rise above a temperature at which the pharmacologically active ingredient (A), preferably the opioid, to be processed may be damaged. Preferably, the temperature of the mixture to be extruded is adjusted to below 180° C., preferably below 150° C., but at least to the softening temperature of polyalkylene oxide (C). Typical extrusion temperatures are 120° C. and 130° C.

In a preferred embodiment, the extruder torque is within the range of from 30 to 95%. Extruder torque can be adjusted inter alia by die geometry, temperature profile and extrusion speed.

After extrusion of the molten mixture and optional cooling of the extruded strand or extruded strands, the extrudates are preferably singulated. This singulation may preferably be performed by cutting up the extrudates by means of revolving or rotating knives, water jet cutters, wires, blades or with the assistance of laser cutters.

Preferably, intermediate or final storage of the optionally singulated extrudate or the final shape of the pharmaceutical dosage form according to the invention is performed under oxygen-free atmosphere which may be achieved, e.g., by means of oxygen-scavengers.

The singulated extrudate may be press-formed into tablets in order to impart the final shape to the pharmaceutical dosage form.

The application of force in the extruder onto the at least plasticized mixture is adjusted by controlling the rotational speed of the conveying device in the extruder and the geometry thereof and by dimensioning the outlet orifice in such a manner that the pressure necessary for extruding the plasticized mixture is built up in the extruder, preferably immediately prior to extrusion. The extrusion parameters which, for each particular composition, are necessary to give rise to a pharmaceutical dosage form with desired mechanical properties, may be established by simple preliminary testing.

For example but not limiting, extrusion may be performed by means of a twin-screw-extruder type ZSE 18 or ZSE 27 (Leistritz, Nürnberg, Germany), screw diameters of 18 or 27 mm. Screws having eccentric ends may be used. A heatable die with a round bore having a diameter of 7, 8, or 9 mm may be used. The extrusion parameters may be adjusted e.g. to the following values: rotational speed of the screws: 120 Upm; delivery rate 2 kg/h for a ZSE 18 or 8 kg/h for a ZSE 27; product temperature: in front of die 125° C. and behind die 135° C.; and jacket temperature: 110° C.

Preferably, extrusion is performed by means of twin-screw-extruders or planetary-gear-extruders, twin-screw extruders (co-rotating or contra-rotating) being particularly preferred.

The pharmaceutical dosage form according to the invention is preferably produced by thermoforming with the assistance of an extruder without any observable consequent discoloration of the extrudates.

The process for the preparation of the pharmaceutical dosage form according to the invention is preferably performed continuously. Preferably, the process involves the extrusion of a homogeneous mixture of all components. It is particularly advantageous if the thus obtained intermediate, e.g. the strand obtained by extrusion, exhibits uniform properties. Particularly desirable are uniform density, uniform distribution of the active compound, uniform mechanical properties, uniform porosity, uniform appearance of the surface, etc. Only under these circumstances the uniformity of the pharmacological properties, such as the stability of the release profile, may be ensured and the amount of rejects can be kept low.

A further aspect of the invention relates to a packaging containing a pharmaceutical dosage form according to the invention and an oxygen scavenger. Suitable packages include blister packages and bottles, such as glass bottles or bottles made from thermoplastic polymers.

Suitable oxygen scavengers are known to the skilled artisan. The oxygen scavenger can be any scavenger known in the art to scavenge oxygen. Both organic and inorganic oxygen scavengers can be used.

In one embodiment, the oxygen scavenger is any metal complex exhibiting oxygen scavenging activity. Examples include complexes containing one or more of aluminum, aluminum ferrosilicon, antimony, beryllium, calcium silicon, cerium, cobalt, gallium, hafnium, iron, magnesium alloy, nickel catalyst, selenium, silicon, silver, strontium, titanium, zinc, and/or zirconium.

In yet another embodiment, one or more elements from Group IA of the periodic table and their alloys and compounds may be used as oxygen scavengers. Examples of Group IA elements include cesium, lithium, potassium, sodium. Further examples of inorganic oxygen scavengers include one or more of sodium azide ($NaN_3$), sodium sulfite ($Na_2SO_3$), hydrazine, and hydroxylamine.

In one embodiment, the oxygen scavenger is an organic compound. Examples include one or more of the polyterpenes, ascorbic acid, amino polycarboxylic acid, cyclohexanedione, tetramethyl piperidone, and heterocyclic compounds with N-substituted amino groups.

Oxygen scavengers and the application thereof in pharmaceutical packaging are known to the skilled artisan. In a preferred embodiment, the oxygen scavenger is selected from the group consisting of metal-catalyzed oxidizable organic polymers and anti-oxidants. Particularly preferred are those oxygen scavengers that are able to perform in a dry environment of below 60% relative humidity, preferably below 30% relative humidity and that are combined with a dessicant. Examples of commercially available oxygen scavengers satisfying these requirements include Pharmakeep® KD10 and KD20.

It has been surprisingly found that the storage stability of the pharmaceutical dosage form can be increased when keeping the oxygen content of the atmosphere within the packaging low. Methods for packaging pharmaceutical dosage forms and the application of suitable oxygen scavengers are known to the skilled artisan. In this regard it can be referred to e.g. D. A. Dean, Pharmaceutical Packaging Technology, Taylor & Francis, 1st ed.; F. A. Paine et al., Packaging Pharmaceutical and Healthcare Products, Springer, 1st ed.; and O. G. Piringer et al., Plastic Packaging: Interactions with Food and Pharmaceuticals, Wiley-VCH, 2nd ed.

As far as the packaging is concerned, round bottles made from polyolefins, preferably from HDPE, are preferred. The thickness of the bottle wall is preferably at least 0.25 mm, more preferably at least 0.5 mm, otherwise the bottle may collapse.

As far as the lid of the packaging is concerned, the packaging is preferably induction or heat-sealed with an aluminium foil.

It has been surprisingly found that by selecting an appropriate shape of the packaging and sealing, the vacuum that is produced by the effect of the oxygen scavenger (underpressure of about 20,000 Pa=2 $N/cm^2$) can be handled without causing a collapse of the packaging. Induction sealing (e.g. 3 seconds energy) is preferred. When sealing a 75 ml bottle having an opening with a diameter of 1 inch with aluminium foil, an underpressure of 20,000 Pa due to oxygen scavenging results in a force of about 10 N corresponding to the force that is exerted by a weight of 1 kg.

The mechanical stability of the sealing can be tested either by introducing an appropriate amount of oxygen scavenger in the bottle, sealing it and waiting for a sufficient period of time, e.g. 2 days, so that the oxygen is scavenged and an underpressure of about 20,000 Pa has been developed. Alternatively, the bottle may be sealed without any oxygen scavenger in its interior and a weight of 1 kg can be placed on the aluminium foil externally thus, simulating the force.

A further aspect of the invention relates to the use of a pharmacologically active ingredient (A), preferably an opioid, for the manufacture of the pharmaceutical dosage form as described above for the treatment of pain.

A further aspect of the invention relates to the use of a pharmaceutical dosage form as described above for avoiding or hindering the abuse of the pharmacologically active ingredient (A), preferably the opioid, contained therein.

A further aspect of the invention relates to the use of a pharmaceutical dosage form as described above for avoiding or hindering the unintentional overdose of the opioid (A) contained therein.

In this regard, the invention also relates to the use of a pharmacologically active ingredient (A), preferably an opioid, as described above and/or a polyalkylene oxide (C) as described above for the manufacture of the pharmaceutical dosage form according to the invention for the prophylaxis and/or the treatment of a disorder, thereby preventing an overdose of the pharmacologically active ingredient (A), preferably the opioid, particularly due to comminution of the pharmaceutical dosage form by mechanical action.

Further, the invention relates to a method for the prophylaxis and/or the treatment of a disorder comprising the administration of the pharmaceutical dosage form according to the invention, thereby preventing an overdose of the pharmacologically active ingredient (A), preferably the opioid, particularly due to comminution of the pharmaceutical dosage form by mechanical action. Preferably, the mechanical action is selected from the group consisting of chewing, grinding in a mortar, pounding, and using apparatuses for pulverizing conventional pharmaceutical dosage forms.

The following examples further illustrate the invention but are not to be construed as limiting its scope.

EXAMPLE 1

Tablets were prepared by hot-melt extrusion of various homogeneous constituent mixtures under the following, identical extrusion conditions:

extruder type: Leistritz Extruder ZSE18PH 40D equipped with high shear screws and a die of 9 mm diameter throughput: 1.0 kg/h revolution velocity: 100 rpm barrel temperature: 100° C.

extrudate temperature: 120° C.

The extrudate was cut into slices of 325 mg containing about 5 mg oxymorphone hydrochloride.

The individual constituents of the extruded mixtures as well as the total amount of decomposition products before and after storage under accelerated storage conditions are summarized in the table here below:

| ex. | (A) | constituents (wt.-%) PEO | PEG | HPMC | α-toc. | further ingredient (wt.-%) | decomposition products (wt.-%) oNo$^1$ | oNo$^2$ | Σ$^1$ | Σ$^2$ |
|---|---|---|---|---|---|---|---|---|---|---|
| A$_1$ | 1.5 | 76.9 | 10.0 | 10.0 | 1.5 | / | 0.06 | 0.58 | 0.41 | 1.93 |
| A$_2$ | 1.5 | 77.5 | 10.0 | 10.0 | 1.0 | / | 0.09 | 0.49 | 0.58 | 1.81 |
| A$_3$ | 1.5 | 78.0 | 10.0 | 10.0 | 0.5 | / | 0.08 | 0.36 | 0.56 | 1.64 |
| A$_4$ | 1.5 | 78.3 | 10.0 | 10.0 | 0.2 | / | 0.08 | 0.26 | 0.63 | 1.51 |
| A$_5$ | 1.5 | 78.5 | 10.0 | 10.0 | 0.0 | / | 0.07 | 0.17 | 0.81 | 1.69 |
| B$_1$ | 1.5 | 76.9 | 10.0 | 10.0 | 1.5 | / | 0.06 | 0.58 | 0.41 | 1.93 |
| B$_2$ | 1.5 | 40.0 | 10.0 | 46.9 | 1.5 | / | 0.09 | 0.55 | 0.64 | 1.76 |
| B$_3$ | 1.5 | 50.0 | 10.0 | 36.9 | 1.5 | / | 0.00 | 0.52 | 0.29 | 1.64 |
| B$_4$ | 1.5 | 50.0 | 36.9 | 10.0 | 1.5 | / | 0.11 | 0.76 | 0.36 | 1.74 |
| C$_1$ | 1.5 | 76.9 | 10.0 | 10.0 | 1.5 | / | 0.06 | 0.58 | 0.41 | 1.93 |
| C$_2$ | 1.5 | 76.9 | / | 10.0 | 1.5 | 10.00 Lutrol ® F68 | 0.05 | 0.53 | 0.65 | 1.83 |
| C$_3$ | 1.5 | 50.0 | 10.0 | 10.0 | 1.5 | 26.90 mannitol | 0.08 | 0.82 | 0.39 | 2.72 |
| C$_4$ | 1.5 | 76.9 | / | 10.0 | 1.5 | 10.00 carnaubawax | 0.12 | 0.53 | 0.39 | 1.03 |
| D$_1$ | 1.5 | 76.9 | 10.0 | 10.0 | 1.5 | / | 0.06 | 0.58 | 0.41 | 1.93 |
| D$_2$ | 1.5 | 76.8 | 10.0 | 10.0 | 1.5 | 0.10 fumaric acid | 0.05 | 0.48 | 0.52 | 1.70 |
| D$_3$ | 1.5 | 76.8 | 10.0 | 10.0 | 1.5 | 0.10 Na-EDTA | 0.07 | 0.51 | 0.48 | 1.77 |
| D$_4$ | 1.5 | 76.8 | 10.0 | 10.0 | 1.5 | 0.10 citric acid | 0.07 | 0.48 | 0.37 | 1.45 |
| E$_1$ | 1.5 | 76.9 | 10.0 | 10.0 | 1.5 | / | 0.06 | 0.58 | 0.41 | 1.93 |
| E$_2$ | 1.5 | 76.8 | 10.0 | 10.0 | 1.5 | 0.10 citric acid | 0.07 | 0.48 | 0.37 | 1.45 |
| E$_3$ | 1.5 | 76.7 | 10.0 | 10.0 | 1.5 | 0.20 citric acid | 0.00 | 0.40 | 0.20 | 1.13 |
| E$_4$ | 1.5 | 76.4 | 10.0 | 10.0 | 1.5 | 0.50 citric acid | 0.00 | 0.06 | 0.12 | 0.17 |

(A): oxymorphone hydrochloride
PEO: polyethylene oxide M$_w$ 7 mio g/mol
PEG: polyethylene glycol 6000
HPMC: hypromellose 100,000 Pa*s
α-toc.: α-tocopherol
oNo: oxymorphone-N-oxide (mixture)
Σ: sum of all impurities
$^1$after extrusion, before storage
$^2$after storage, amber glass bottles, plastic cap, 4 weeks, 40° C., 75% rel. humidity The decomposition products were analyzed by HPLC-UV. The elution peak for oxymorphone-N-oxide could not be sufficiently base-line separated from a peak of an unknown degradation product (called "UK 0.83"). Thus, both peaks were jointly integrated. It becomes evident from a comparison of examples A$_1$ to A$_5$ that the content of oxymorphone-N-oxide before storage (oNo$^1$) is not substantially changed when the content of antioxidant α-tocopherol is decreased from 1.5 wt.-% to 1.0 wt.-%, 0.5 wt.-%, 0.2 wt.-% and even 0 wt.-%. Upon storage (oNo$^2$), however, the content of oxymorphone-N-oxide is proportional to the content of α-tocopherol. This is most surprising because oxymorphone-N-oxide is an oxidation product and one would expect that antioxidants usually rather suppress than support the formation of oxidation products.

Nonetheless, the complete omission of antioxidant (α-tocopherol) can have disadvantages. It could be shown by viscosity measurements (in the absence of acid (B)) that the high molecular polyethylene oxide is degraded upon extrusion and/or storage in the absence of antioxidant. However, it has now been surprisingly found that to a certain extent the acid (B) in turn can compensate such degradation so that in certain embodiments antioxidants can be omitted or the content thereof can be substantially decreased.

It has been surprisingly found that about 0.2 wt.-% α-tocopherol suffice in order to stabilize the polyethylene oxide; higher contents of α-tocopherol do not result in higher viscosities of the polyalkylene oxide and, thus, do not prevent PEO more pronounced from degradation. Thus, the content of antioxidant (α-tocopherol) is preferably balanced so that on the one side, the high molecular weight polyethylene oxide is sufficiently stabilized and that on the other side, the undesired formation of oxymorphone-N-oxide is kept low during storage.

Further, it becomes evident from a comparison of examples B$_1$ to B$_4$ and examples C$_1$ to C$_4$ that the partial replacement of the high molecular weight polyethylene oxide or the total replacement of the polyethylene glycol by an alternative plasticizer does not result in a substantial decrease of the content of undesired oxymorphone-N-oxide. This is surprising because one would expect that polyethylene oxide and polyethylene glycol are potential peroxide carriers and that a reduction thereof would result in a reduction of oxidative processes such as the oxidation of oxymorphone to oxymorphone-N-oxide.

Still further, it becomes evident from a comparison of examples D$_1$ to D$_5$ and E$_1$ to E$_4$ that the addition of physiologically acceptable acids, particularly citric acid, leads to a reduction of the formation of oxymorphone-N-oxide. This effect is more pronounced when the amount of acid is increased. At a concentration of 0.1 wt.-%, the effect is comparatively weak, but at a concentration of 0.2 wt.-% the effect is stronger and is further enhanced when the concentration of citric acid is increased. Not only the amount of oxymorphone-N-oxide is decreased, but also the total amount of decomposition products, particularly of those having high HPLC retention times.

EXAMPLE 2

Tablets that had been manufactured in analogy to ex. A$_1$, B$_1$, C$_1$, D$_1$ and E$_1$ above were packaged in different packaging materials and stored at 40° C. and 75% rel. humidity. The decomposition products before and after storage under accelerated storage conditions are summarized in the table here below:

|  | closed HDPE, sealed with aluminium foil | | | open amber glass | | closed amber glass + oxygen scavenger | | closed amber glass + desiccant | | closed amber glass + argon | |
| --- | --- | --- | --- | --- | --- | --- | --- | --- | --- | --- | --- |
|  | before storage 323.64 mg | 4 weeks 324.05 mg | 8 weeks 325.57 mg | 4 weeks 323.56 mg | 8 weeks 337.25 mg | 4 weeks 325.23 mg | 8 weeks 322.65 mg | 4 weeks 321.27 mg | 8 weeks 322.69 mg | 4 weeks 324.62 mg | 8 weeks 324.30 mg |
| content oxymorphone | 96.30% | 92.90% | 89.40% | 93.70% | 88.50% | 96.70% | 94.80% | 94.60% | 92.50% | 94.60% | 92.50% |
| purity oxymorphone | 99.18% | 97.70% | 96.70% | 98.03% | 94.50% | 99.10% | 98.62% | 98.59% | 97.98% | 98.36% | 98.04% |
| content α-tocopherol | 91.69% | 91.51% | 90.89% | 93.51% | 79.94% | 94.52% | 93.62% | 90.56% | 88.23% | 93.51% | 92.18% |
| oxymorphone-N-oxide | 0.09% | 0.64% | 1.16% | 0.19% | 0.53% | 0.03% | 0.04% | 0.15% | 0.24% | 0.17% | 0.30% |
| UK 0.83 | 0.00% | 0.00% | 0.00% | 0.36% | 2.15% | 0.06% | 0.08% | 0.32% | 0.77% | 0.00% | 0.00% |
| Sum of oxymorphone-N-oxide and UK 0.83 | 0.09% | 0.64% | 1.16% | 0.55% | 2.63% | 0.09% | 0.12% | 0.37% | 1.01% | 0.17% | 0.30% |
| main unknown | 0.13% | 0.38% | 0.43% | 0.45% | 2.15% | 0.16% | 0.18% | 0.32% | 0.77% | 0.46% | 0.34% |
| Sum of impurities Σ | 0.73% | 2.22% | 3.21% | 1.88% | 5.44% | 0.82% | 0.95% | 1.33% | 1.94% | 1.55% | 1.88% |

HDPE bottles had a volume of 75 ml. The oxygen scavenger was Pharmakeep ® KD20 (Mitsubishi, Japan).

It has been surprisingly found that inclusion of an oxygen scavenger in the packaging results in a further stabilization of the dosage form so that the formation of decomposition products is limited to extremely low values.

EXAMPLE 3

Tablets were manufactured as described in example 1, packed into HDPE bottles of 75 ml volume together with an oxygen scavenger combined with a desiccant (Pharmakeep 20 KD), closed with a plastic cap with induction seal.

The individual constituents of the extruded mixtures, the total amount of decomposition products before and after storage under accelerated storage conditions are summarized in the table here below:

The results reveal that the purity of the product is very high after manufacturing and that the product exhibit stable during 8 weeks storage under accelerated conditions of 40° C./75% rel. humidity.

EXAMPLE 4

Tablets were manufactured as described in example 1 but cut into slices of 215 mg representing 5 mg or 40 mg of oxymorphone HCl, after forming the tablets were coated with about 6.5 mg each of a conventional Opadry II film-coat containing polyvinylalcohol as the film forming excipient, packed into HDPE bottles of 75 ml volume together with an oxygen scavenger combined with a desiccant (Pharmakeep 20 KD), closed with a plastic cap with induction seal.

The individual constituents of the extruded mixtures, the total amount of decomposition products before and after storage under accelerated storage conditions are summarized in the table here below:

| | constituents (wt-%) | | | | | | decomposition products (wt.-%) | | | | | |
| --- | --- | --- | --- | --- | --- | --- | --- | --- | --- | --- | --- | --- |
| ex | (A) | PEO | PEG | HPMC | α-toc. | Citric acid | oNo$^1$ | oNo$^2$ | oNo$^3$ | Σ$^1$ | Σ$^2$ | Σ$^3$ |
| F$_1$ | 1.5 | 73.8 | 10.0 | 14.0 | 0.2 | 0.5 | nd | nd | nd | nd | nd | 0.05 |
| F$_2$ | 1.5 | 77.8 | 10.0 | 10.0 | 0.2 | 0.5 | nd | nd | nd | nd | 0.05 | 0.10 |

(A): oxymorphone hydrochloride
PEO: polyethylene oxide M$_w$ 7 mio g/mol
PEG: polyethylene glycol 6000
HPMC: hypromellose 100,000 Pa*s
α-toc.: α-tocopherol
oNo: oxymorphone-N-oxide (mixture)
Σ: sum of all impurities
[1]after extrusion, before storage
[2]after storage, HDPE bottles, plastic cap with induction seal, oxygen scavenger, 4 weeks, 40° C., 75% rel. humidity
[3]after storage, HDPE bottles, plastic cap with induction seal, oxygen scavenger, 8 weeks, 40° C., 75% rel. humidity

| ex. | constituents (wt.-%) | | | | | | decomposition products (wt.-%) | | | |
|---|---|---|---|---|---|---|---|---|---|---|
| | (A) | PEO | PEG | HPMC | α-toc. | Citric acid | oNo[1] | oNo[2] | Σ[1] | Σ[2] |
| $G_1$ | 2.33 | 70.0 | 16.63 | 10.0 | 0.2 | 0.84 | nd | nd | nd | nd |
| $G_2$ | 18.6 | 56.8 | 13.56 | 10.0 | 0.2 | 0.84 | nd | nd | 0.05 | 0.05 |

(A): oxymorphone hydrochloride
PEO: polyethylene oxide $M_w$ 7 mio g/mol
PEG: polyethylene glycol 6000
HPMC: hypromellose 100,000 Pa*s
α-toc.: α-tocopherol
oNo: oxymorphone-N-oxide (mixture)
Σ: sum of all impurities
[1] after extrusion, before storage
[2] after storage, HDPE bottles, plastic cap with induction seal, oxygen scavenger, 1 month, 40° C., 75% rel. humidity

EXAMPLE 5

The most preferred dosage form according to example 3 is also suitable for the stabilization of oxycodone. This could be demonstrated for a formulation containing 80 mg of oxycodone HCl manufactured analogue to example 1 but, the extrudate was cut into slices of 400 mg:

| ex. | constituents (wt.-%) | | | | | | decomposition products (wt.-%) | | | |
|---|---|---|---|---|---|---|---|---|---|---|
| | (A) | PEO | PEG | HPMC | α-toc. | Citric acid | oNo[1] | oNo[2] | Σ[1] | Σ[2] |
| $H_1$ | 20 | 54.3 | 15 | 10 | 0.2 | 0.5 | 0.06 | 0.07 | 0.22 | 0.13 |

(A): oxycodone
PEO: polyethylene oxide $M_w$ 7 mio g/mol
PEG: polyethylene glycol 6000
HPMC: hypromellose 100,000 Pa*s
α-toc.: α-tocopherol
oNo: oxycodone-N-oxide (Impurity D + E)
[1] after extrusion, before storage
[2] after storage, amber glass bottles, plastic cap, oxygen scavenger with desiccant (Pharmakeep 20 KD) 1 month, 40° C., 75% rel. humidity

EXAMPLE 6

In a single dose (40 mg oxymorphone HCl, tablets of example 4), randomized, three-way crossover study with 1 week between treatments subjects were fasted overnight and meals were served 4 and 10 hours after dosing. No water was given within ±1 hour of dosing. All tablets were taken with 240 mL of water (example T).

PK samples were taken for oxymorphone and 6-OH-oxymorphone predose and up through 48 hours after dosing.

Bioequivalence was compared to Opana ER® (reference R).

The results are summarized in the tables here below:

| | Treatment | Mean | SD | CV |
|---|---|---|---|---|
| $C_{max}$ [pg/mL] | T | 2147 | 989 | 46% |
| | R | 2671 | 1163 | 44% |
| AUCT [pg * h/mL] | T | 38695 | 13836 | 36% |
| | R | 38171 | 14652 | 38% |
| AUC [pg * h/mL] | T | 42575 | 15836 | 37% |
| | R | 41296 | 15242 | 37% |

| | Point Estimate T/R | Lower Limit 90% CI | Upper Limit 90% CI |
|---|---|---|---|
| $C_{max}$ | 79.37 | 71.69 | 87.87 |
| AUCT | 101.98 | 95.17 | 109.29 |
| AUC | 102.24 | 95.48 | 109.48 |

CI = confidence interval

It becomes evident that the dosage forms according to the invention having an increased breaking strength are bioequivalent to conventional dosage forms (Opana ER®).

EXAMPLE 7

Tablets were prepared under identical conditions by hot-melt extrusion of two homogeneous constituent mixtures $I_1$ and $I_2$:

| | $I_1$ | $I_2$ |
|---|---|---|
| Oxymorphone HCl [%] | 11.1 | 11.1 |
| PEO [%] | 68.2 | 63.2 |
| PEG [%] | 10.0 | 15.0 |
| HPMC Shin Etsu [%] | 10.0 | 10.0 |
| α-tocopherol [%] | 0.2 | 0.2 |
| Citric acid, anhydrous [%] | 0.5 | 0.5 |
| Tablet weight [mg] | 360 | 360 |
| PEO:PEG | 6.82:1 | 4.21:1 | under the following, identical extrusion conditions:
 extruder type: Leistritz Extruder type Micro 27 GL 40 D equipped with medium shear screws and a die of 8 mm diameter
 throughput: 10 kg/h
 revolution velocity: 120 rpm
 manufacturing time: 30 min
 temperature of hottest heating zone: 100° C.
 die temperature: 130° C.

The extrudate was cut into slices of 360 mg containing about 40 mg oxymorphone hydrochloride.

100 slices were weighed individually and the standard deviation of weight was calculated. Slices of composition $I_1$ (PEO:PEG=6.82:1) showed a standard deviation of 2.3%, whereas slices of composition $I_2$ (PEO:PEG=4.21:1) showed a standard deviation of 1.6% only.

It becomes evident from these comparative tests that surprisingly, the processability of the extruded mass can be improved by adjusting the ratio of PEO to PEG.

EXAMPLE 8

In order to investigate if also multicarboxylic acids other than citric acid could hamper the formation of oxymorphone-N-oxide, tablets containing maleinic acid or fumaric acid were manufactured as described in example 1. For comparison, also tablets containing the inorganic salt $NaH_2PO_4$ were manufactured. The samples were stored in open dishes at 40° C. and 75% relative humidity for 4 weeks.

The individual constituents of the extruded mixtures as well as the total amount of decomposition products before and after storage under accelerated storage conditions are summarized in the table here below:

|     | constituents (wt.-%) | | | | | further | decomposition products (wt.-%) | | | |
| --- | --- | --- | --- | --- | --- | --- | --- | --- | --- | --- |
| ex. | (A) | PEO | PEG | HPMC | α-toc. | ingredient (wt.-%) | oNo$^1$ | oNo$^2$ | Σ$^1$ | Σ$^2$ |
| J$_1$ | 1.5 | 76.0 | 10.0 | 10.0 | 1.5 | Maleinic acid 1.0% | nd | nd | 0.20 | 0.22 |
| J$_2$ | 1.5 | 76.0 | 10.0 | 10.0 | 1.5 | Fumaric acid 1.0% | nd | nd | 0.17 | 0.30 |
| J$_3$ | 1.5 | 76.0 | 10.0 | 10.0 | 1.5 | NaH$_2$PO$_4$ 1.0 %* | nd | 0.18 | 0.06 | 0.75 |

(A): oxymorphone hydrochloride
PEO: polyethylene oxide M$_w$ 7 mio g/mol
PEG: polyethylene glycol 6000
HPMC: hypromellose 100,000 Pa*s
α-toc.: α-tocopherol
*NaH$_2$PO$_4$: Used in form of 1.3% of the di-hydrate
oNo: oxymorphone-N-oxide (mixture)
Σ: sum of all impurities; maleinic acid, fumaric acid and related compounds subtracted from sum of impurities
$^1$after extrusion, before storage
$^2$after storage, open dish, 4 weeks, 40° C., 75% rel. humidity In case of maleinic and fumaric acid these compounds and for maleinic acid another related compound were detected during the purity tests as impurities (up to about 40%). Their values have been subtracted from the sum of impurities.

It becomes evident from a comparison of examples J$_1$ and J$_2$ to A$_1$ and B$_1$ that the presence of maleinic and fumaric acid protected oxymorphone totally against oxidation to N-oxide and to a large extent against other degradation although the samples were stored in open dishes and not in closed bottles. These results are comparable to those obtained with citric acid (example 1, D$_4$ and E$_2$-E$_4$). Samples containing NaH$_2$PO$_4$ (J$_3$) exhibited protection against N-oxide formation and other degradation when compared to the formulations without any acidic compound (A$_1$ and B$_1$) but to a less extent than the multicarboxylic acids like citric, maleinic and fumaric acid.

EXAMPLE 9

In order to investigate if the presence of citric acid also protects oxidation sensitive opioids other than oxymorphone against N-oxidation, tablets containing oxycodone hydrochloride were manufactured as described in example 1.

For comparison, also tablets containing smaller amounts of α-tocopherol were manufactured. The samples were stored in open dishes at 40° C. and 75% relative humidity for 4 weeks.

The individual constituents of the extruded mixtures as well as the total amount of decomposition products before and after storage under accelerated storage conditions are summarized in the table here below:

|     | constituents (wt.-%) | | | | | further | decomposition products (wt.-%) | | | |
| --- | --- | --- | --- | --- | --- | --- | --- | --- | --- | --- |
| ex. | (A) | PEO | PEG | HPMC | α-toc. | ingredient (wt.-%) | oNo$^1$ | oNo$^2$ | Σ$^1$ | Σ$^2$ |
| K$_1$ | 1.5 | 77.0 | 10.0 | 10.0 | 1.5 | / | 0.05 | 0.58 | 0.31 | 1.63 |
| K$_2$ | 1.5 | 78.3 | 10.0 | 10.0 | 0.2 | / | 0.05 | 0.28 | 0.58 | 0.69 |

-continued

| ex. | constituents (wt.-%) | | | | further ingredient (wt.-%) | decomposition products (wt.-%) | | | |
|---|---|---|---|---|---|---|---|---|---|
| | (A) | PEO | PEG | HPMC | α-toc. | | oNo[1] | oNo[2] | Σ[1] | Σ[2] |
| $K_3$ | 1.5 | 76.0 | 10.0 | 10.0 | 1.5 | Citric acid 1.0 | nd | nd | 0.19 | 0.22 |
| $K_4$ | 1.5 | 77.3 | 10.0 | 10.0 | 0.2 | Citric acid 1.0 | nd | nd | 0.18 | 0.23 |

(A): oxycodone hydrochloride
PEO: polyethylene oxide $M_w$ 7 mio g/mol
PEG: polyethylene glycol 6000
HPMC: hypromellose 100,000 Pa*s
α-toc.: α-tocopherol
oNo: oxycodone-N-oxide
Σ: sum of all impurities
[1] after extrusion, before storage
[2] after storage, open dish, 4 weeks, 40° C., 75% rel. humidity These results show that citric acid protected oxycodone totally against oxidation to the N-oxide and to a large extent against other degradation although the samples were stored in open dishes rather than in closed bottles. Reducing the amount of α-tocopherol resulted in reduced degradation, when formulations were employed not containing citric acid. These results are comparable to those obtained with oxymorphone.

EXAMPLE 10

In accordance with Example 1, tablets containing tramadol HCL were manufactured from the following compositions:

| | $L_1$ | $L_2$ | $L_3$ | $L_4$ |
|---|---|---|---|---|
| Tramadol HCl [%] | 13.3 | 13.3 | 13.3 | 13.3 |
| PEO [%] | 61.0 | 61.7 | 61.2 | 61.5 |
| PEG [%] | 15.0 | 15.0 | 15.0 | 15.0 |
| HPMC [%] | 10.0 | 10.0 | 10.0 | 10.0 |
| a-tocopherol [%] | 0.2 | — | — | 0.2 |
| Citric acid, anhydrous [%] | 0.5 | — | 0.5 | — |
| Tablet weight [mg] | 600 | 600 | 600 | 600 |
| PEO:PEG | 4.07:1 | 4.11:1 | 4.08:1 | 4.10:1 |

The dissolution profile of the tablets was investigated under the following conditions: Paddle apparatus equipped with sinker, 75 rpm, 37° C., 600 mL simulated intestinal fluid pH 6.8 (phosphate buffer). The release profile of tramadol was detected spectrometrically at 271 nm.

The results are displayed in FIG. 1.

The tablets according to example $L_2$ show the fastest dissolution which is about 20% faster than that of the slow releasing tablets according to examples $L_1$ and $L_4$ after 480 minutes. The release from tablets according to $L_3$ is faster than those two batches, but still about 6% slower than from tablets according to $L_2$ after 480 minutes.

This is surprising as a big influence of the presence of α-tocopherol on the dissolution profile is observed. This particularly surprising given that the role of the α-tocopherol in the formulation is to act as an antioxidant for the prevention of polymer degradation. Interestingly the presence of citric acid compensates for a small part of this effect.

EXAMPLE 11

By swelling of a tablet according to examples $L_1$ (Example 10) in an appropriate amount of water, a homogeneous gel was obtained. Accordingly, tablets according to examples $L_2$ to $L_4$ were swelled in the same amount of water, i.e. under identical conditions, to obtain the respective gels. The viscosity of each gel was measured next as an indirect measure for the polymer chain length of the ethylene oxide contained therein. The viscosity measurements were conducted by means of a rotational viscometer at a shear rate of 40 s$^{-1}$.

| | α-Tocopherol | Citric acid | Viscosity (mPas) |
|---|---|---|---|
| $L_1$ | + | + | 381 |
| $L_2$ | − | − | 67 |
| $L_3$ | − | + | 154 |
| $L_4$ | + | − | 337 |

Compared to the dissolution profiles of example 10, the same ranking was obtained: The formulation according to example $L_2$ exhibited the lowest viscosity, while the formulations according to examples $L_1$ and $L_4$ exhibited the highest viscosity. The formulation according to example $L_3$ exhibited a significantly lower viscosity than the two high viscosity formulations but is still superior to formulation $L_2$.

The higher viscosity of the formulations $L_1$ and $L_4$ is an indication for a higher average polymer chain length of the polyethylene oxide contained therein. Apparently, the polyethylene oxide contained in formulations $L_1$ and $L_4$ has less been affected by oxidative degradation in the course of manufacture of the dosage form than formulations $L_2$ and $L_3$.

Summarizing the results of the dissolution profile (Example 10) measurements and the viscosity determinations, it can be concluded that the increase in dissolution velocity is based on more pronounced polymer degradation during the manufacturing for the batches without α-tocopherol (examples $L_2$ and $L_3$).

These results show that acid (B), e.g. citric acid, also has a protective effect on the polymer during manufacturing. Formulation $L_3$ which does not contain any α-tocopherol but citric acid shows a higher viscosity and lower acceleration of dissolution in comparison to the formulation $L_2$ which contains neither α-tocopherol nor citric acid.

The invention claimed is:

1. A tamper-resistant pharmaceutical dosage form in form of a tablet having a breaking strength of at least 300 N thermoformed by hot-melt extrusion of a mixture comprising the following components: a pharmacologically active ingredient (A) selected from the group consisting of oxymorphone and physiologically acceptable salts thereof; citric acid in an amount of from 0.5 wt.-% to 5.0 wt.-%, based on the total weight of the pharmaceutical dosage form; α-tocopherol in an amount of from 0.001 wt.-% to 5.0 wt.-%, based on the total weight of the pharmaceutical dosage form; wherein the weight ratio of citric acid to α-tocopherol being in a range of from 4.2:1 to 1:3; and a polyalkylene oxide (C) having a weight average molecular weight $M_w$ of at least 500,000 to 15,000,000 g/mol, the polyalkylene oxide (C) being present in the pharmaceutical dosage form in an amount of 56.8-77.8 wt.-% based on the total weight of the pharmaceutical dosage form and wherein the polyalkylene oxide (C) is polyethylene oxide.

2. The pharmaceutical dosage form according to claim 1, wherein after storage for 4 weeks at 40° C. and 75% rel. humidity, the content of pharmacologically active ingredient (A) amounts to at least 98.0% of its original content before storage.

3. The pharmaceutical dosage form according to claim 1, wherein after storage for 4 weeks at 40° C. and 75% rel. humidity, the content of the polyethylene oxide (C) amounts to at least 98.0% of its original content before storage.

4. The pharmaceutical dosage form according to claim 1, wherein the pharmacologically active ingredient (A) is embedded in a matrix comprising the polyalkylene oxide (C), said matrix controlling the release of the pharmacologically active ingredient (A) from the pharmaceutical dosage form.

5. The pharmaceutical dosage form according to claim 1, which is adapted for administration once daily or twice daily.

6. The pharmaceutical dosage form according to claim 1, which has a breaking strength of at least 500 N.

7. A packaging containing a pharmaceutical dosage form according to claim 1 and an oxygen scavenger.

8. A process for the production of the pharmaceutical dosage form according to claim 1 comprising the steps:
   a) mixing the components of claim 1 to form a resultant mixture;
   b) heating the resultant mixture in an extruder at least up to the softening point of the polyalkylene oxide (C) of claim 1 and extruding extrudate through the outlet orifice of the extruder by application of force,
   c) singulating the extrudate to yield singulated extrudate and forming into the pharmaceutical dosage form, or
   d) cooling and optionally reheating the singulated extrudate and forming it into the pharmaceutical dosage form.

9. A method of treating pain in a patient in need of such treatment, said method comprising administering to said patient a pharmaceutical dosage form according to claim 1.

* * * * *